United States Patent
Zhai et al.

(10) Patent No.: US 11,298,339 B2
(45) Date of Patent: Apr. 12, 2022

(54) BISDIAZABICYCLO COMPOUND FOR TREATMENT AND/OR PREVENTION OF HEPATITIS VIRUS-RELATED DISEASES OR DISORDERS

(71) Applicants: JIANGSU ASCENTAGE BIOMED DEVELOPMENT INC., Jiangsu (CN); HEALTHQUEST PHARMA INC., Guangdong (CN)

(72) Inventors: Yifan Zhai, Guangzhou (CN); Xiaoyong Zhang, Guangzhou (CN); Jinlin Hou, Guangzhou (CN); Dajun Yang, Taizhou (CN)

(73) Assignees: JIANGSU ASCENTAGE BIOMED DEVELOPMENT INC., Taizhou (CN); HEALTHQUEST PHARMA INC., Guangzhou (CN)

( * ) Notice: Subject to any disclaimer, the term of this patent is extended or adjusted under 35 U.S.C. 154(b) by 0 days.

(21) Appl. No.: 16/624,050

(22) PCT Filed: Nov. 20, 2018

(86) PCT No.: PCT/CN2018/116289
§ 371 (c)(1),
(2) Date: Dec. 18, 2019

(87) PCT Pub. No.: WO2019/101047
PCT Pub. Date: May 31, 2019

(65) Prior Publication Data
US 2021/0290594 A1    Sep. 23, 2021

(30) Foreign Application Priority Data
Nov. 24, 2017 (CN) .......................... 201711193388.1

(51) Int. Cl.
*A61K 31/33* (2006.01)
*A61K 31/40* (2006.01)
(Continued)

(52) U.S. Cl.
CPC ............ *A61K 31/407* (2013.01); *A61K 47/54* (2017.08); *A61K 47/55* (2017.08); *A61P 31/20* (2018.01)

(58) Field of Classification Search
CPC ..... A61K 31/551; A61K 31/407; A61P 31/20; A61P 31/14
(Continued)

(56) References Cited

U.S. PATENT DOCUMENTS

2014/0057924 A1*  2/2014  Wang ................... A61K 31/496
                                                    514/254.08
2016/0143995 A1*  5/2016  Pellegrini .......... A61K 38/1761
                                                    424/85.1

FOREIGN PATENT DOCUMENTS

CN       101484151 A     7/2009
CN       102378762 A     3/2012
(Continued)

OTHER PUBLICATIONS

Ringehan et al. ("Viral hepatitis and liver cancer," Phil. Trans. R. Soc. B, Sep. 2017, 372: 20160274 https://www.ncbi.nlm.nih.gov/pmc/articles/PMC5597741/pdf/rstb20160274.pdf). (Year: 2017).*
(Continued)

*Primary Examiner* — Shengjun Wang
(74) *Attorney, Agent, or Firm* — McCarter & English, LLP; Wei Song

(57) ABSTRACT

Disclosed are a bisdiazabicyclo compound for treating and/or preventing hepatitis virus-related diseases or disorders, a method for treating and/or preventing hepatitis virus-related diseases or disorders by using the bisdiazabicyclo com-
(Continued)

pound, and a use of the bisdiazabicyclo compound in the preparation of a drug for treating and/or preventing hepatitis virus-related diseases or disorders, and/or eliminating or mitigating hepatitis virus-related diseases or disorders.

5 Claims, 9 Drawing Sheets

(51) Int. Cl.
   *A61K 31/407* (2006.01)
   *A61K 47/55* (2017.01)
   *A61K 47/54* (2017.01)
   *A61P 31/20* (2006.01)

(58) Field of Classification Search
   USPC .................................... 514/221, 183, 413
   See application file for complete search history.

(56) References Cited

FOREIGN PATENT DOCUMENTS

| CN | 104718209 A | 6/2015 |
|---|---|---|
| CN | 107987083 A | 5/2018 |
| WO | 2007/130626 A2 | 11/2007 |
| WO | 2010/117704 A1 | 10/2010 |
| WO | 2011/050068 A2 | 4/2011 |
| WO | 2014/031487 A1 | 2/2014 |
| WO | 2014/205516 A1 | 12/2014 |
| WO | 2015/109391 A1 | 7/2015 |
| WO | 2016/172134 A2 | 10/2016 |
| WO | 2017/011590 A1 | 1/2017 |

OTHER PUBLICATIONS

Ebert et al., Cellular inhibitor of apoptosis proteins prevent clearance of hepatitis B virus. Proc Natl Acad Sci U S A. May 5, 2015;112(18):5797-802.

Sheng et al., A potent bivalent Smac mimetic (SM-1200) achieving rapid, complete, and durable tumor regression in mice. J Med Chem. May 23, 2013;56(10):3969-79.

International Search Report and Written Opinion for Application No. PCT/CN2018/116289, dated Feb. 26, 2019, 22 pages.

* cited by examiner

BISDIAZABICYCLO COMPOUND FOR TREATMENT AND/OR PREVENTION OF HEPATITIS VIRUS-RELATED DISEASES OR DISORDERS

CROSS-REFERENCE TO RELATED APPLICATIONS

This application is an U.S. national stage application of PCT International Application No. PCT/CN2018/116289, filed on Nov. 20, 2018, which claims the benefit of foreign priority of Chinese Patent Application No. 201711193388.1, filed on Nov. 24, 2017. The entire contents of the aforementioned applications are incorporated herein by reference.

TECHNICAL FIELD

The present invention relates to a diazabicyclo compound for the treatment and/or prevention of a disease or disorder associated with a hepatitis virus, a method of using the same to treat and/or prevent a disease or disorder associated with a hepatitis virus, and a use of the same in the manufacture of a medicament for the treatment and/or prevention of a disease or disorder associated with a hepatitis virus or for the elimination and/or alleviation of a disease or disorder associated with a hepatitis virus.

BACKGROUND ART

Hepatitis or liver disease is usually caused by hepatitis virus. Hepatitis viruses generally are divided into the following types: A, B, C, D, E and G, in which hepatitis B virus causes chronic diseases that are currently distributed worldwide and a considerable proportion of hepatitis B may turn into liver cancer in the later stage of disease development if it is not improperly controlled. There are currently an estimated 280,000,000 hepatitis B patients (or HBV carriers) worldwide.

According to the Guideline of Prevention and Treatment for Chronic Hepatitis B (CHB) 2015 version in China, the goal of chronic hepatitis B treatment is to maximize the long-term inhibition of HBV replication, reduce inflammatory necrosis of liver cells and liver fibrosis, and delay and reduce liver failure and decompensation of liver cirrhosis, HCC and other complications, thereby improving quality of life and extending survival time. In the treatment process, for some suitable patients, the clinical cure of chronic hepatitis B should be pursued as much as possible, that is, after the end of treatment, there should be continuous virological response, HBsAg negative conversion or accompanied by anti-HBs positive conversion, normal ALT, mild or no lesions of liver tissues. The complete healing means that except antibodies, HBV DNA, various antigens, and cccDNA are eliminated in body.

At present, many international guidelines for the prevention and treatment of chronic hepatitis B take the negative conversion of surface antigen (HBsAg) (also known as functional cure) as an ideal target for CHB antiviral therapy. However, although the existing antiviral drugs such as interferons (Interferon alpha, IFN-α) and nucleos(t)ide analogues [NUCs] can inhibit viral replication, the clearance or seroconversion of HBsAg may hardly occur within a limited or long-term course of treatment. Currently, there are 7 antiviral drugs approved by the FDA for the treatment of chronic hepatitis B infection, including ordinary and pegylated interferons and 5 oral nucleos(t)ide analogs (i.e., lamivudine, adefovir dipivoxil, entecavir, telbivudine, and tenofovir disoproxil fumarate (TDF)), in which entecavir (ETV) and tenofovir disoproxil fumarate are recommended as therapeutic first-line drugs (Liaw, Leung et al. 2008; Lok and McMahon 2009; Liu, Yang et al. 2014; Gish, Given et al. 2015). However, after the clinical use of existing NUCs drugs for 5 years, the HBsAg negative conversion ratio was less than 5%; and for those showing response after receiving pegylated interferon (PEG-IFN) treatment, the HBsAg negative conversion ratio was less than 10% during long-term follow-up (Sundaram and Kowdley 2015). For the patients with CHB, NUCs drugs can only inhibit the synthesis of the viral positive and negative strands in nucleocapsids; during the antiviral therapy thereof, the mainly disappeared thing is replication DNA, and there is no direct effect on the cccDNA in the nucleus of liver cells and the viral antigens transcribed and expressed thereby (Wong, Seto et al. 2013). Another class of drugs, IFNα, has both immunoregulatory and direct antiviral effects, and can induce the expression of APOBEC3A in HBV-infected liver cells, promote the degradation of cccDNA through base editing, and exert direct antiviral effects (Lucifora, Xia et al. 2014). However, it has been confirmed that HBV can antagonize the IFNα signaling pathway, resulting in poor therapeutic effect of IFNα drugs (Bertoletti and Ferrari 2012). Therefore, given the limitations of current antiviral drugs, other therapeutic strategies such as stimulating and/or restoring antiviral immunity are currently hot-spots in researches for the clearance of chronic HBV infection (Lucifora and Trepo 2015).

A host-specific immune response is essential for HBV clearance. The HBV-specific T-lymphocyte response is the most important effector cell to clear HBV infection in liver cells. After HBV infects and enters liver cells through sodium ion/taurocholate cotransporting polypeptide receptor, the viral genome can be repaired by host DNA polymerase to form a stable covalently closed circular DNA (cccDNA) and parasitized in nucleus of the liver cells. As the original template for viral replication and gene expression in the liver, the difficulty in removal of cccDNA microchromosomes is an important reason for the difficulty of cure in clinical antiviral treatment (Nassal 2015). HBV effector T cells can directly kill infected liver cells, induce target cell apoptosis, and clear cccDNA and other viral products through the killing effects of granzymes, perforin, or the cytotoxic pathway of hepatocyte apoptosis induced by FasL (Hoh, Heeg et al. 2015). In addition, cytokines such as IFNγ and TNFα secreted by effector T cells can also affect infected liver cells and induce intracellular antiviral gene expression through non-cytolytic pathway to inhibit viral replication and cccDNA synthesis (Guidotti, Rochford et al. 1999). The latest research suggests that the effector T cells can be anchored to the hepatic sinusoids through platelets, and directly contact infected liver cells presenting viral antigens through the endothelial cell gap, and then secrete cytokines such as IFNγ and TNFα to directly induce the apoptosis of the infected liver cells so as to clear HBV (Guidotti, Inverso et al. 2015). Furthermore, the B cells also play a very important role in controlling HBV infection. In acute HBV infection, the hepatitis B surface antigen antibody (HBsAb) produced by B cells can neutralize and block HBV infection of liver cells.

IAP proteins are a key class of apoptosis regulators and are characterized by the presence of one or more BIR (baculovirus IAP repeat) domains. Among IAPs, cellular IAP1 (cIAP1) and cIAP2 play a key role in the regulation of death receptor-mediated apoptosis, while X-linked IAP (XIAP) inhibits death receptor-mediated and mitochondrial-mediated apoptosis by binding and inhibiting caspase-3/7 and caspase-9 (three cysteine proteases that are critical for performing apoptosis). These JAP proteins are highly overexpressed in both cancer cell lines and human tumor tissues, and have low expression in normal cells and tissues. Extensive researches have shown that the overexpression of IAP proteins makes cancer cells resistant to the apoptosis inducted by a variety of anticancer drugs. A detailed discussion of IAP proteins and their effects on cancer as well as apoptosis is described in U.S. Pat. No. 7,960,372.

One category of central negative regulator for apoptosis is inhibitor of apoptosis protein (IAP). This category includes proteins such as XIAP, cIAP1, cIAP2, ML-IAP, HIAP, KIAP, TSIAP, NAIP, survivin, livin, ILP-2, apollon, and BRUCE.

Small molecule inhibitors of IAP proteins are also known. For example, U.S. Patent Publication No. 2005/0197403 and U.S. Pat. No. 7,960,372 disclose dimeric Smac mimetic compounds. Among them, bisdiazabicyclo compounds are a class of compounds that inhibit IAP.

Studies have shown that peptide-based inhibitors are useful tools to elucidate the anti-apoptotic function of IAP and the role of IAP in the response of cancer cells to chemotherapeutic agents. The prior art does not disclose or suggest that the bisdiazabicyclo compounds are effective in inhibiting or eliminating hepatitis viruses, especially HBV viruses.

CONTENTS OF THE INVENTION

In the research, the inventors of the present application unexpectedly found that the bisdiazabicyclo compounds are extremely effective in inhibiting and/or eliminating hepatitis viruses, especially HBV virus.

Accordingly, a first aspect of the present invention relates to a bisdiazabicyclo compound for treatment and/or prevention of a disease or disorder associated with a hepatitis virus, wherein the compound is a bisdiazabicyclo compound. Further, the bisdiazabicyclo compound is a compound having the following structure or a pharmaceutically acceptable salt thereof:

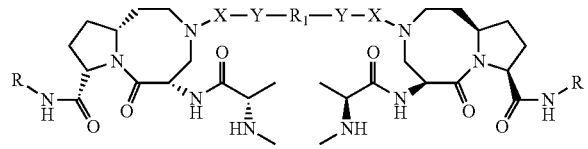

(I)

where X is selected from:

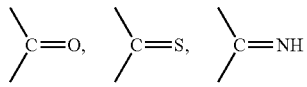

and —SO$_2$—;

Y is selected from —NH—, —O—, —S— and is absent;

R is selected from

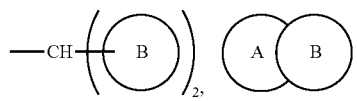

(where the ring A is a $C_{4-8}$ aliphatic ring), —$C_{3-6}$ cycloalkylene

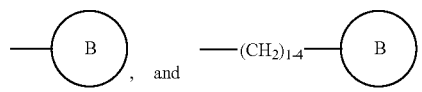

(where the ring B is phenyl, naphthyl, pyridyl, pyridazinyl, pyrazinyl, or pyrimidinyl, and the B ring is optionally substituted);

$R_1$ is selected from

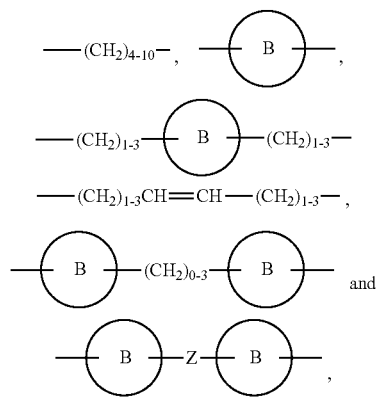

wherein Z is O, S, NH or

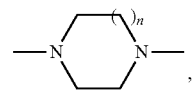

where n is 0, 1 or 2, and wherein the ring B is phenyl, naphthyl, pyridyl, pyridazinyl, pyrazinyl or pyrimidinyl, and the ring B is optionally substituted.

Preferably, in the compound, R is

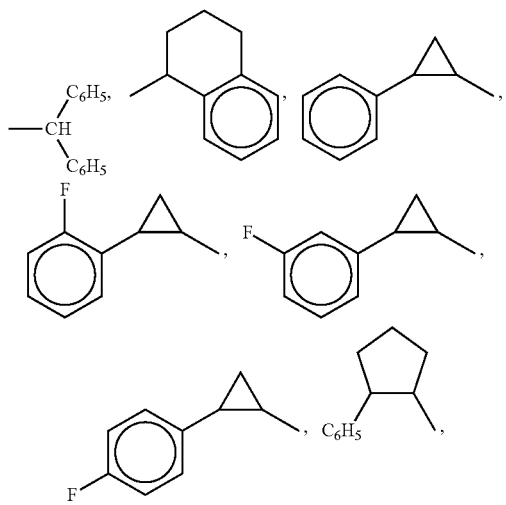

5
-continued
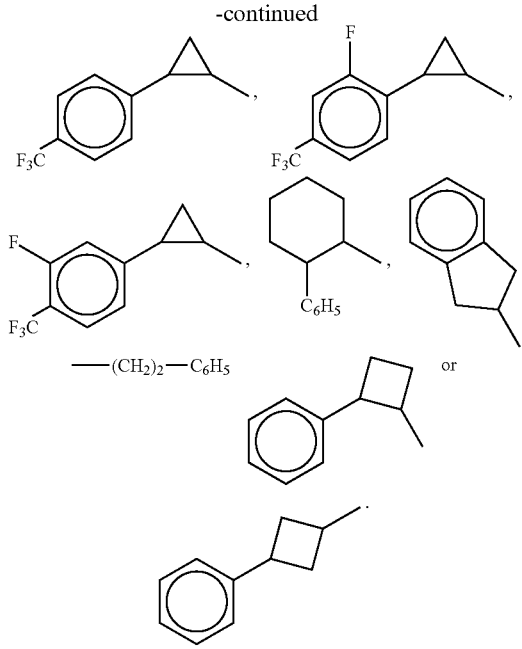
Preferably, in the compound, $R_1$ is
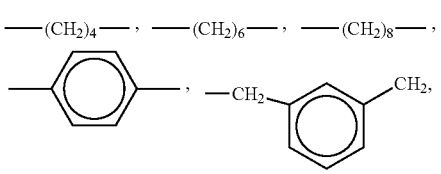
6
-continued
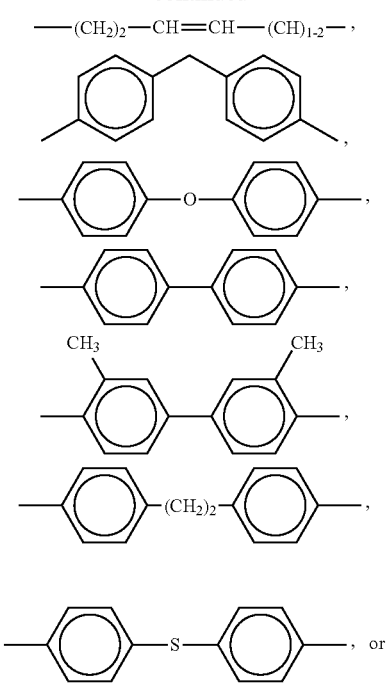
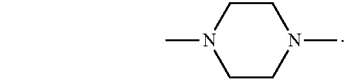
Preferably, in the compound, X is $SO_2$ and Y is absent.
Preferably, the compound is
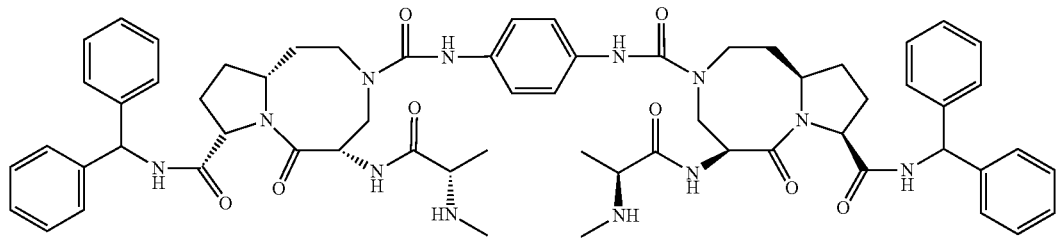
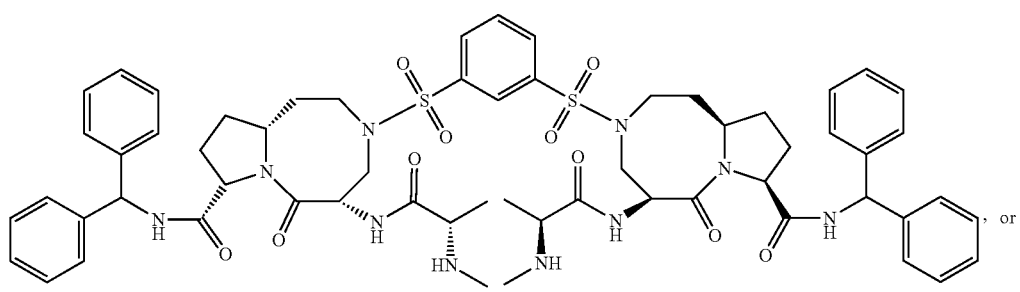, or -continued

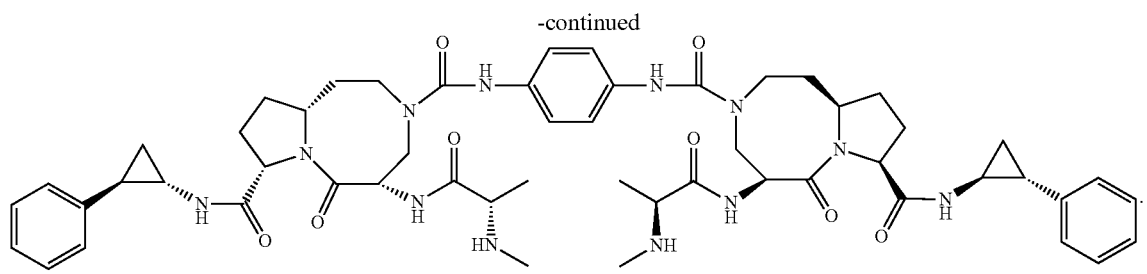

Preferably, the compound is selected from:

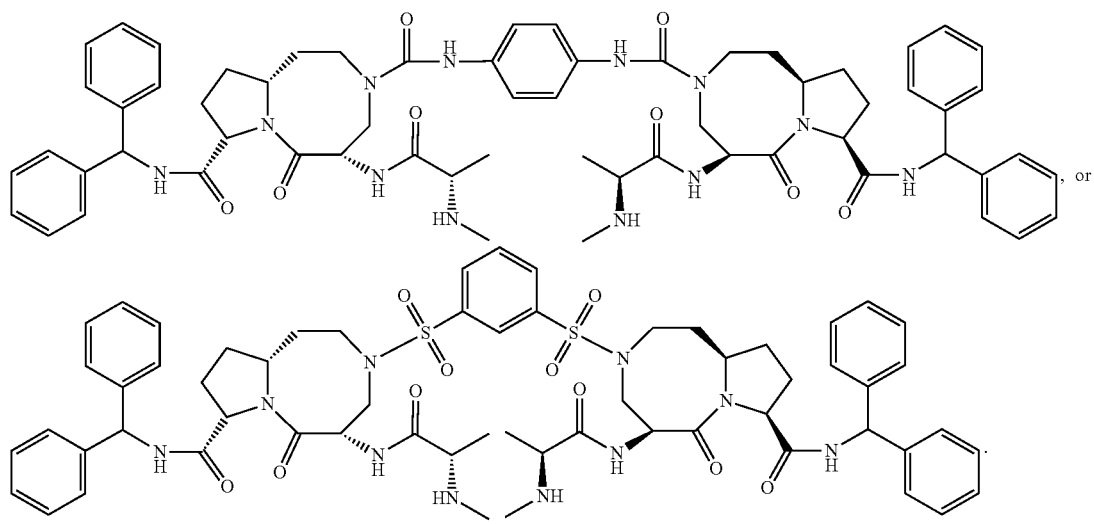

Further, the disease or disorder associated with hepatitis virus is a disease or disorder associated with the late stage of infection with hepatitis virus. Preferably, the disease or disorder associated with hepatitis virus is a disease or disorder associated with hepatitis A virus, hepatitis B virus or hepatitis C virus. More preferably, the hepatitis virus-related disease or disorder includes, but is not limited to: hepatitis A, hepatitis B, hepatitis C, and liver cirrhosis. Further, the compound treats and/or prevents a disease or disorder associated with hepatitis virus by modulating an immune response.

A second aspect of the present invention relates to a use of the compound as defined above in manufacture of a medicament for treatment and/or prevention of a disease or disorder associated with a hepatitis virus.

A third aspect of the present invention relates to a method for treating and/or preventing a disease or disorder associated with a hepatitis virus, comprising administering a therapeutically and/or prophylactically effective amount of the compound to a patient suffering from the disease or disorder associated with the hepatitis virus, and the compound being a bisdiazabicyclo compound.

A fourth aspect of the present invention relates to a pharmaceutical composition comprising the compound as defined above, wherein the pharmaceutic composition is useful in the treatment and/or prevention of a disease or disorder associated with a hepatitis virus.

DESCRIPTION OF FIGURES

FIG. 5 shows the anti-HBV effect of the administration of Compound 1 in combination with IFNα2a in a C57BL/6J mouse model of chronic HBV infection.

FIG. 6 shows the comparison of the anti-HBV effects of Compound 1 and Birinapant in a chronic HBV-infected C57BL/6J mouse model established by high-pressure tail vein injection of pAAV-HBV1.2 plasmid.

FIG. 7 shows the administration of anti-HBV effect of Compound 1 in combination with anti-PD1 antibody in a chronic HBV infection C57BL/6J mouse model established by high-pressure tail vein injection of pAAV-HBV1.2 plasmid.

FIG. 8 shows the anti-HBV effects of Compound 1 and SF18 in a C57BL/6J mouse model established by tail vein injection of rAAV8-HBV1.3 (ayw) virus.

DETAILED DESCRIPTION OF THE INVENTION

Definition

Figure 1:
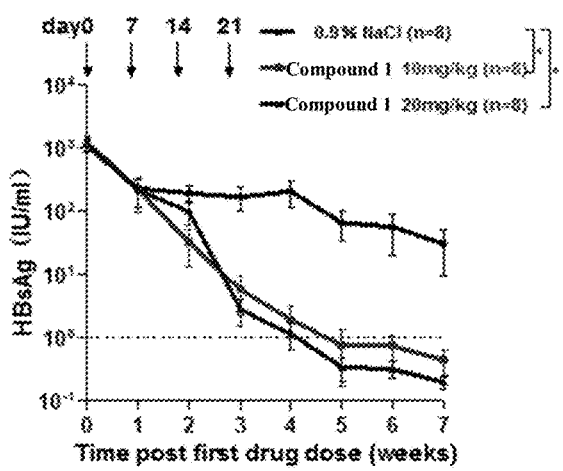
FIG. 1 shows the effect of single-dose injection of Compound 1 on HBV in a C57BL/6J mouse model established by high-pressure tail vein injection of pAAV-HBV1.2 plasmid. A: dynamic changes of HBsAg in serum for each group; B: dynamic changes of HBV DNA in serum for each group; C: HBcAg expression in liver tissue for each group detected in 7 weeks by immunohistochemical staining; D: HBV replication intermediate in liver for each group detected in 7 weeks by Southern Blot.
Figure 1:
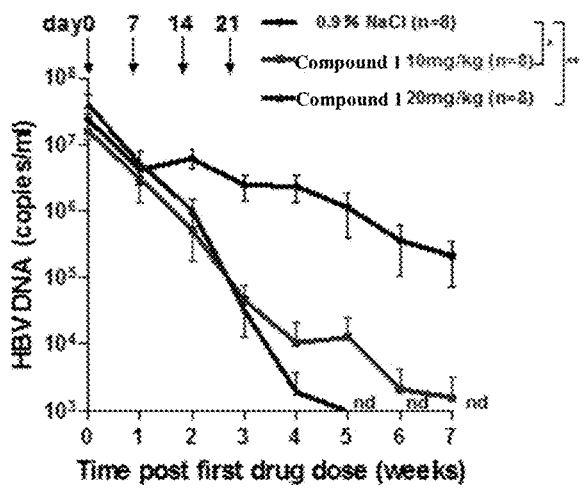
Figure 1:
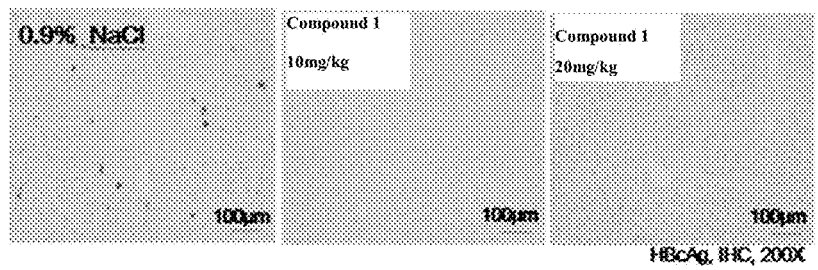
Figure 1:
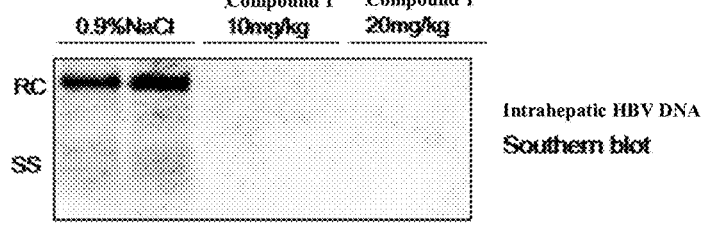

The term "$C_{4-8}$ aliphatic ring" as used herein refers to a cyclobutyl, cyclopentyl, cyclohexyl, cycloheptyl or cyclooctyl unsubstituted or substituted by 1 to 3 groups (e.g., $C_{1-4}$ alkyl, halogen, trifluoromethyl, trifluoromethoxy, hydroxy, alkoxy, nitro, cyano, alkylamino or amino).

The term "alkyl" as used herein refers to a saturated $C_{1-10}$ hydrocarbon group in form of straight- or branched-chain, and its non-limiting examples include methyl, ethyl, and propyl, butyl, pentyl, hexyl, heptyl, octyl, nonyl and decyl in form of straight- or branched-chain.

The term "$C_{3-6}$ cycloalkylene" refers to a disubstituted cycloalkane having 3 to 6 carbon atoms, for example,

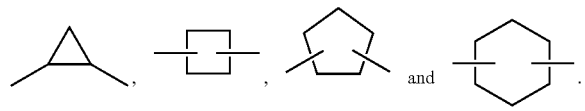

"$C_{3-6}$ cycloalkylene" may be unsubstituted or substituted with 1 to 3 groups, such as $C_{1-4}$ alkyl, halogen, trifluoromethyl, trifluoromethoxy, hydroxy, alkoxy, nitro, cyano, alkylamino or amino.

The term "halogen" as used herein is defined as fluorine, chlorine, bromine or iodine.

The term "hydroxy" as used herein is defined as —OH.

The term "alkoxy" as used herein is defined as —OR, where R is alkyl.

The term "amino" as used herein is defined as —NH₂, and the term "alkylamino" is defined as —NR₂, wherein at least one R is an alkyl group and the second R is an alkyl group or hydrogen.

The term "nitro" as used herein is defined as —NO₂.

The term "cyano" as used herein is defined as —CN.

The term "trifluoromethyl" as used herein is defined as —CF$_3$.

The term "trifluoromethoxy" as used herein is defined as —OCF$_3$.

The term "optionally substituted" as used herein means being substituted with one or more, especially one to four, groups independently selected from, for example, halogen, alkyl, alkenyl, —OCF$_3$, —NO$_2$, —CN, —NC, —OH, alkoxy, amino, alkylamino, —CO$_2$H, —CO$_2$alkyl, alkynyl, cycloalkyl, nitro, mercapto, imino, amido, phosphonate, phosphinate, silyl, alkylthio, sulfonyl, sulfonamido, aldehyde, heterocycloalkyl, trifluoromethyl, aryl and heteroaryl.

The term "aryl" as used herein refers to a monocyclic or polycyclic aromatic group, preferably a monocyclic or bicyclic aromatic group, such as phenyl or naphthyl.

The term "heteroaryl" as used herein refers to a monocyclic or bicyclic ring system containing one or two aromatic rings and containing at least one and up to four nitrogen atoms in one of the aromatic rings.

The term "disease" or "disorder" means a disordered and/or abnormal condition that is generally considered as a pathological state or function, and can manifest itself in the form of specific signs, disorders, and/or malfunctions.

The term "treating" a disease or disorder means eliminating, inhibiting, reducing or alleviating the disease or disorder, and the term "preventing" means avoiding and obviate a disease or disorder, or preventing the disease or disorder from occurring or appearing.

The first aspect of the present invention relates to a bisdiazabicyclo compound, the compound is used for treatment and/or prevention, or elimination and/or alleviation of a disease or disorder associated with a hepatitis virus, wherein the compound is a bisdiazabicyclo compound.

Further, the bisdiazabicyclo compound is a compound having the following structure or a pharmaceutically acceptable salt thereof:

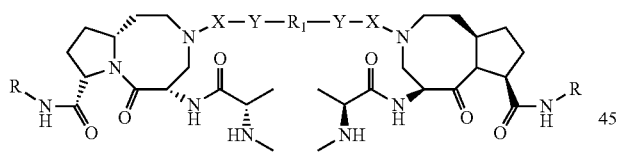
(I)

where X is selected from:

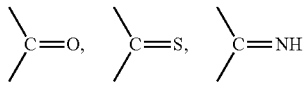

and —SO$_2$—;

Y is selected from —NH—, —O—, —S— and is absent;

R is selected from

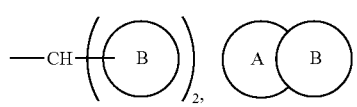

(where the ring A is a C$_{4-8}$ aliphatic ring), —C$_{3-6}$ cycloalkylene

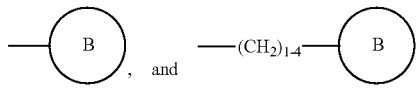

(where the ring B is phenyl, naphthyl, pyridyl, pyridazinyl, pyrazinyl, or pyrimidinyl, and the B ring is optionally substituted);

R$_1$ is selected from

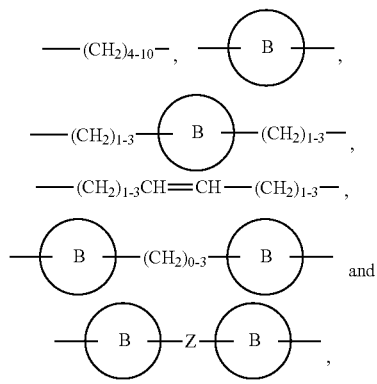

wherein Z is O, S, NH or

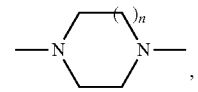

where n is 0, 1 or 2, and wherein the ring B is phenyl, naphthyl, pyridyl, pyridazinyl, pyrazinyl or pyrimidinyl, and the ring B is optionally substituted.

Preferably, in the compound, R is

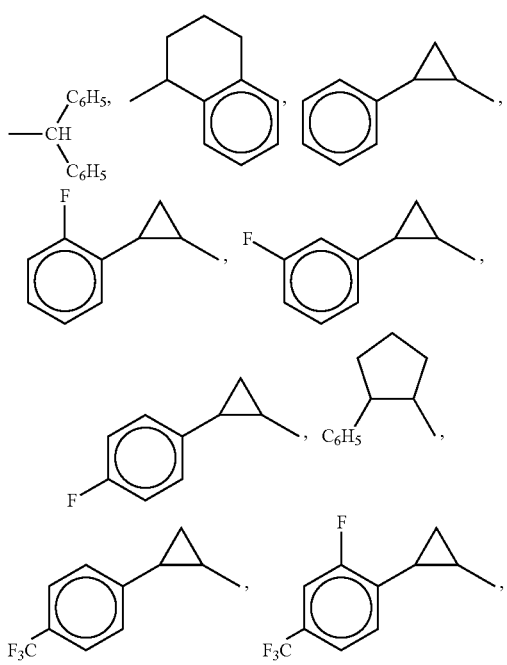

-continued
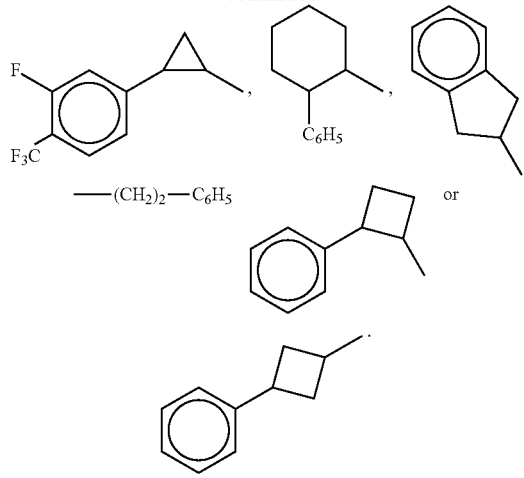
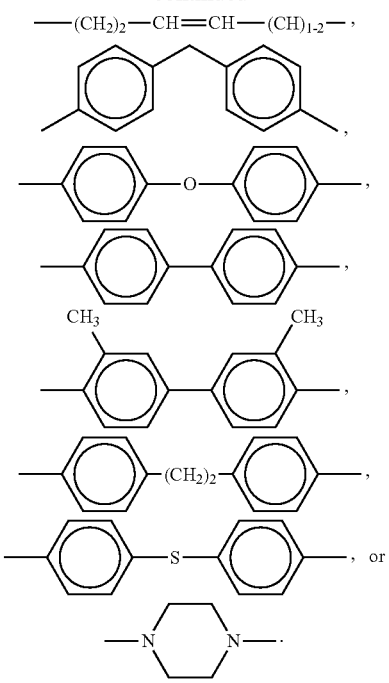
Preferably, in the compound, $R_1$ is
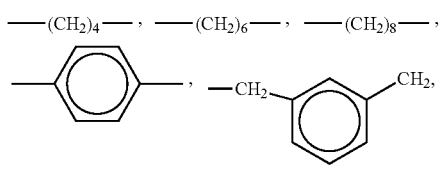
Preferably, in the compound, X is $SO_2$ and Y is absent.
Preferably, the compound is
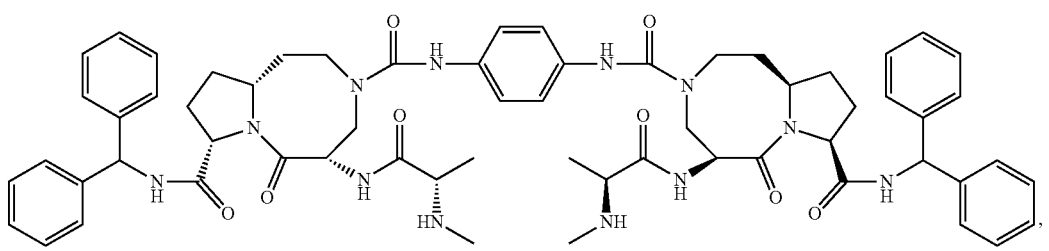,
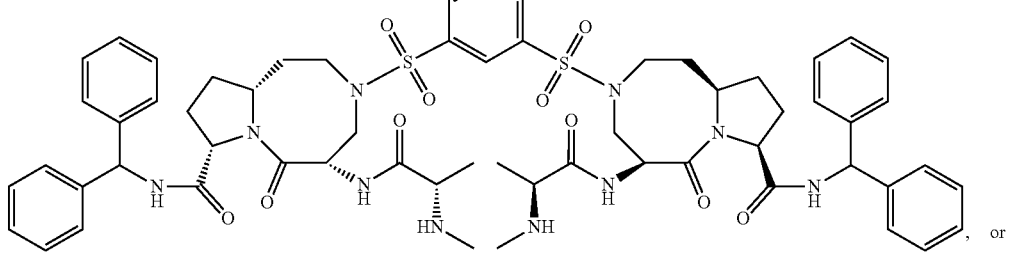, or
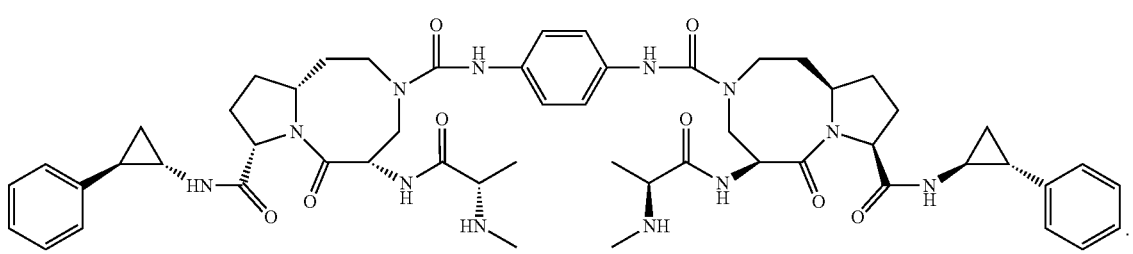.

Further, the bisdiazabicyclo compound is a compound having the following structure or a pharmaceutically acceptable salt thereof:

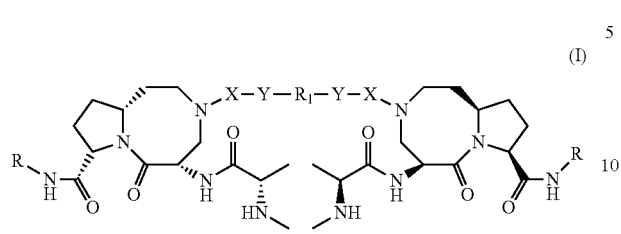
(I)

where X is selected from:

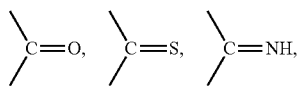

and —SO$_2$—;
Y is selected from —NH—, —O—, —S—, and is absent when X is —SO$_2$—;
R is selected from

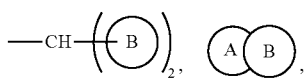

and —C$_{3-6}$ cycloalkylene

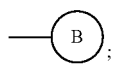

and
R$_1$ is selected from

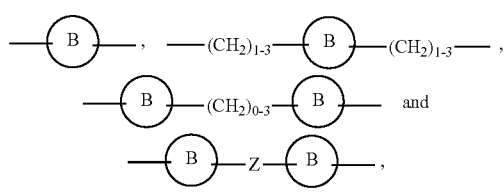

wherein Z is O, S or NH;
wherein the ring A is a C$_{4-8}$ aliphatic ring; and B is phenyl, naphthyl, pyridyl, pyridazinyl, pyrazinyl or pyrimidinyl, and is optionally substituted by 1 to 4 groups independently selected from halogen, —OCF$_3$, —NO$_2$, —CN, —NC, —OH, amino, C$_{1-10}$ alkyl, C$_{1-10}$ alkyloxy, and C$_{1-10}$ alkylamino.
Preferably, in the compound, R is

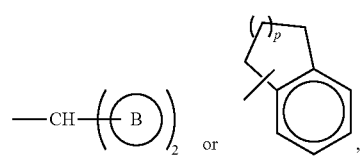

wherein p is 0 to 4.

Preferably, in the compound, R

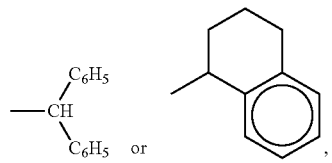

wherein phenyl is optionally substituted by 1 to 4 groups independently selected from halogen, —OCF$_3$, —NO$_2$, —CN, —NC, —OH, amino, C$_{1-10}$ alkyl, C$_{1-10}$ alkyloxy and C$_{1-10}$ alkylamino.
Preferably, in the compound, R is

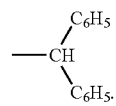

Preferably, in the compound, R$_1$ is

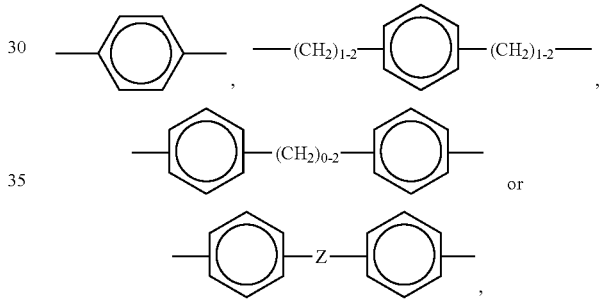

wherein phenyl is optionally substituted by 1 to 4 groups independently selected from halogen, —OCF$_3$, —NO$_2$, —CN, —NC, —OH, amino, C$_{1-10}$ alkyl, C$_{1-10}$ alkyloxy and C$_{1-10}$ alkylamino.
Preferably, in the compound, R$_1$ is

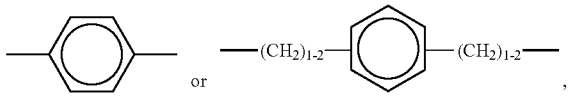

wherein phenyl is optionally substituted by 1 to 4 groups independently selected from halogen, —OCF$_3$, —NO$_2$, —CN, —NC, —OH, amino, C$_{1-10}$ alkyl, C$_{1-10}$ alkyloxy and C$_{1-10}$ alkylamino.
Preferably, in the compound, X is

and Y is —NH—.

17
Preferably, in the compound, X is
and Y is —NH—.
18
Preferably, in the compound, X is
and Y is O.
Preferably, the compound is selected from
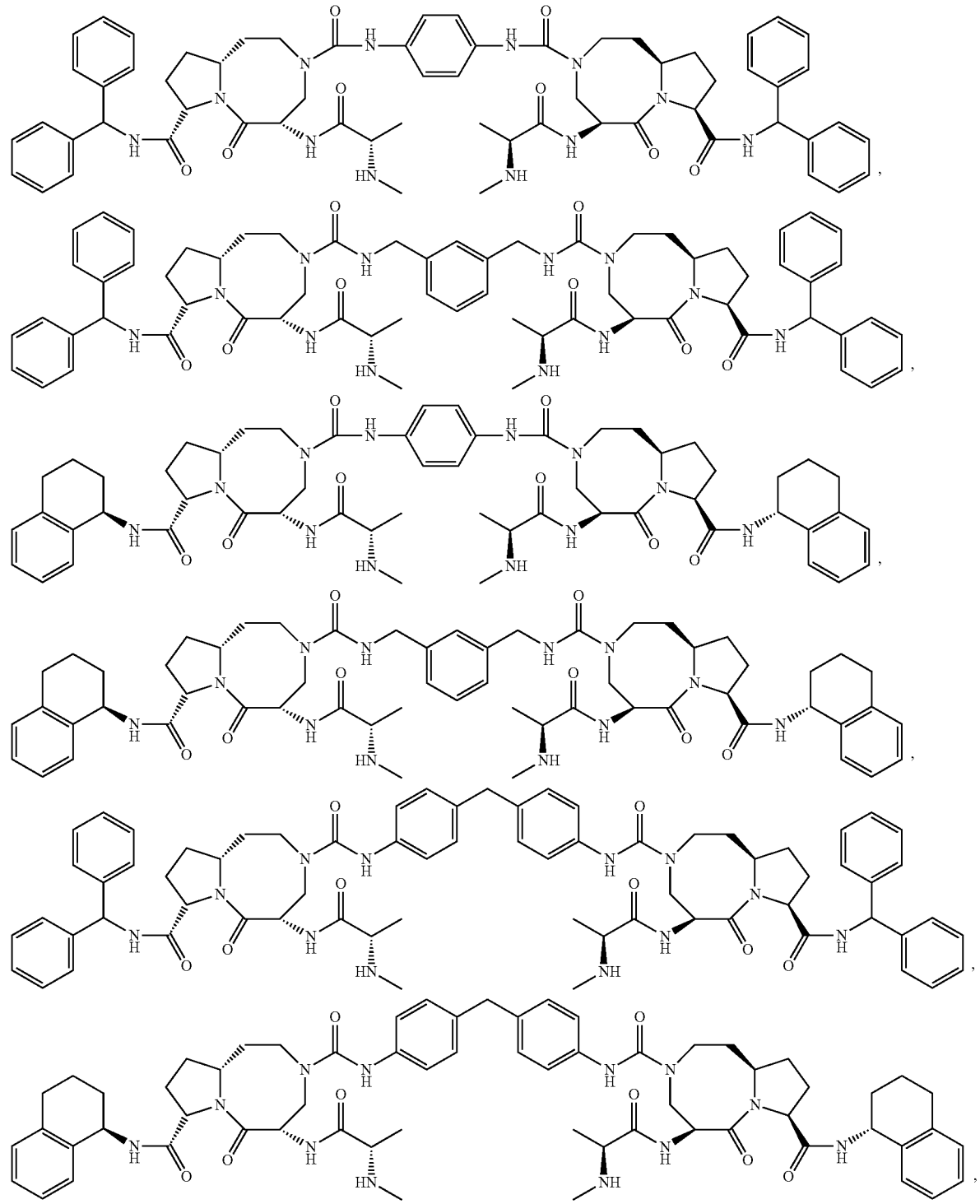

-continued
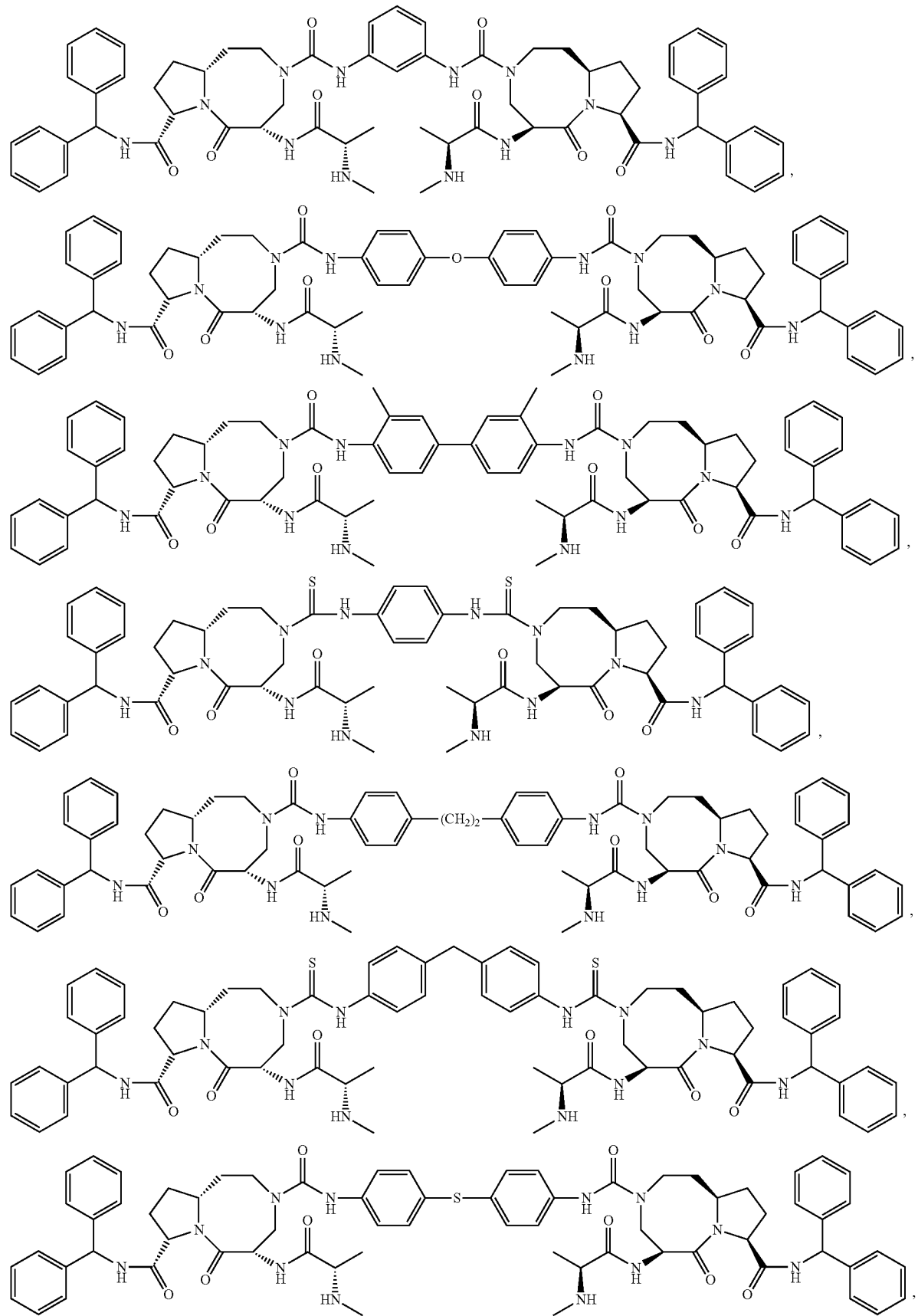

-continued
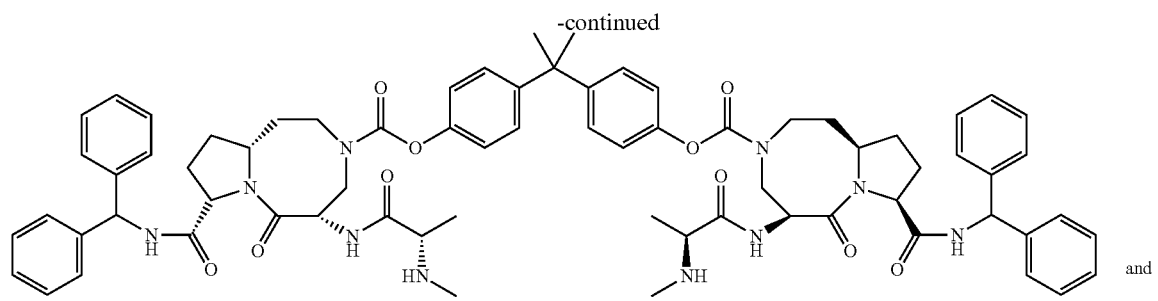
and
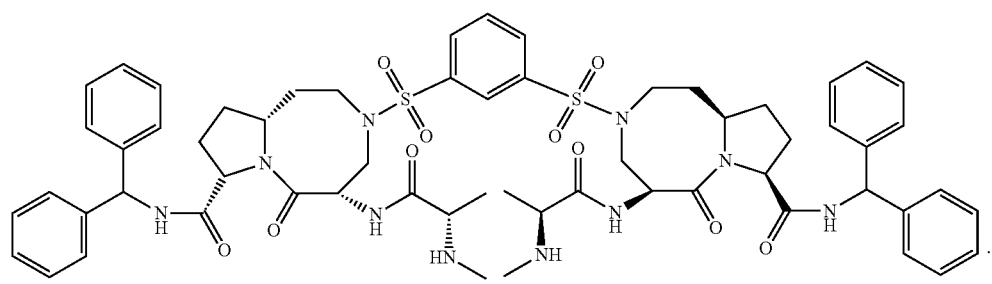
Preferably, the compound is
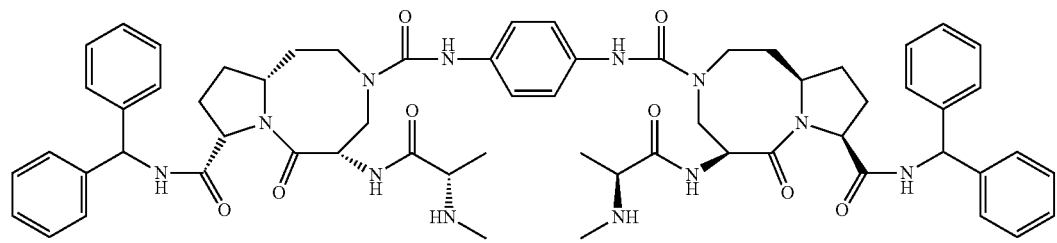
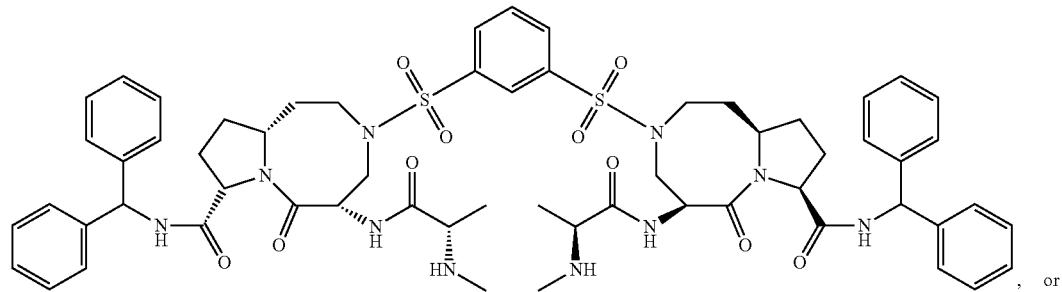
, or
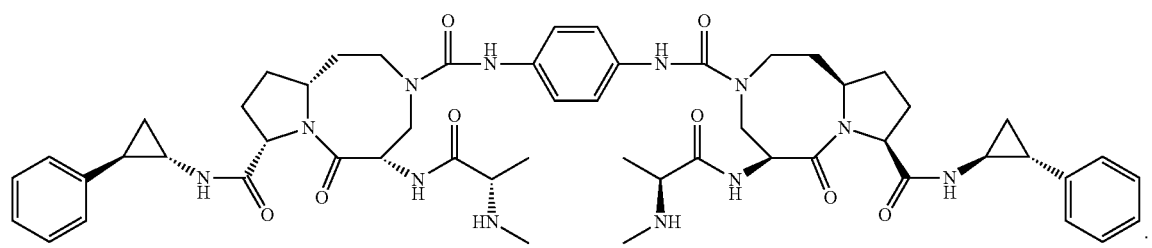
.

Preferably, the compound is selected from

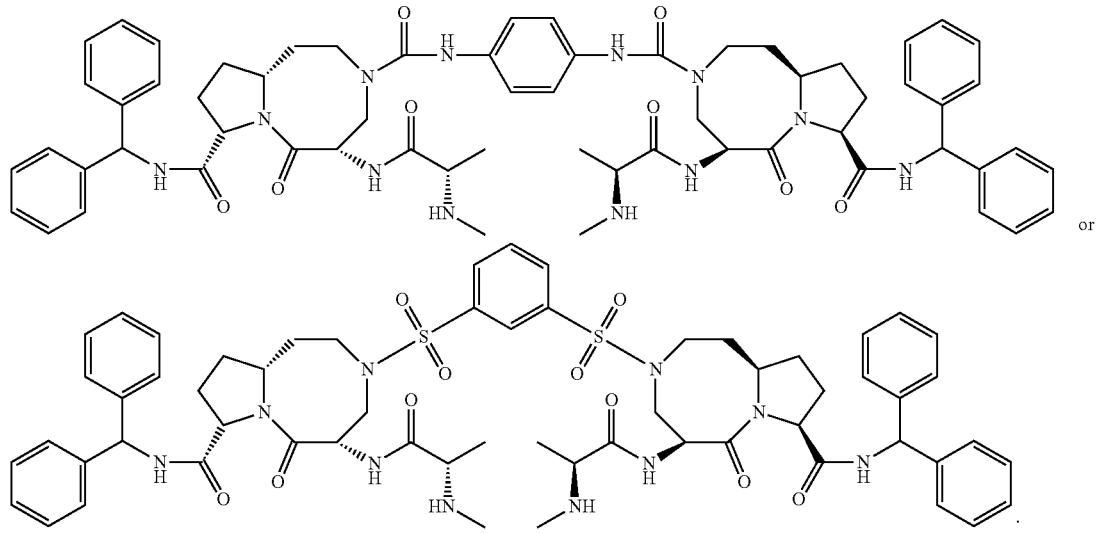

or

Preferably, the compound is SF18, which has the following structure

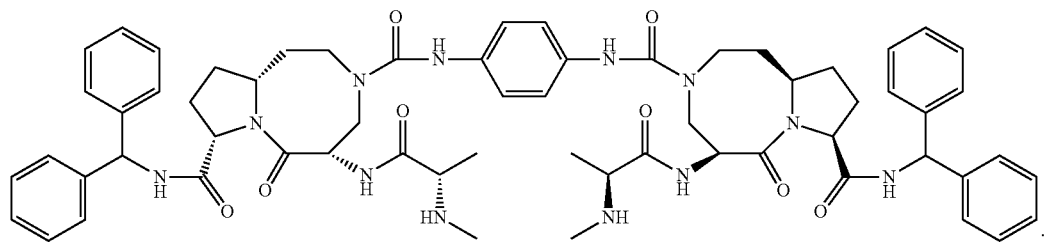 [SMILES: CN[C@@H](C)C(=O)N[C@H]1CN(C(=O)Nc2ccc(NC(=O)N3CC[C@H]4CC[C@@H](C(=O)NC(c5ccccc5)c5ccccc5)N4C(=O)[C@@H](NC(=O)[C@H](C)NC)C3)cc2)CC[C@H]2CC[C@@H](C(=O)NC(c3ccccc3)c3ccccc3)N2C1=O]

Preferably, the compound is Compound 1, that is, 1,3-benzene-di[7-(3S,5S,9aR)-5-((S)-2-methylamino-propionamido)-3-diphenylmethylaminocarbonyl-4-oxo-3a,7-diaza-decahydro-cyclopentanocyclooctene)]-sulfonamide, having the following structure:

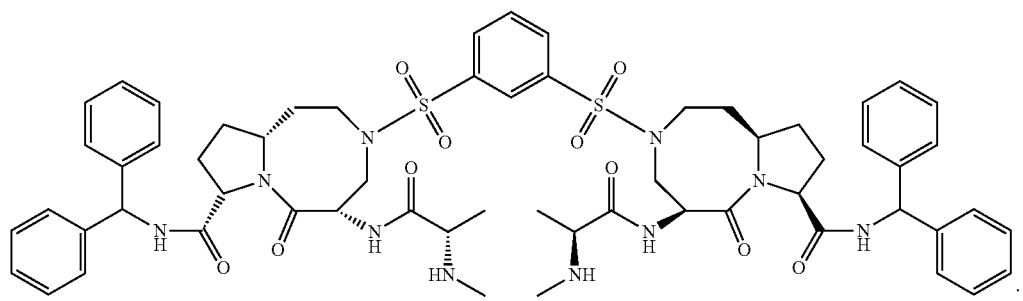

According to the present invention, the compound is obtained according to the preparation method disclosed in PCT/US2013/055384 (WO2014/031487), the entire contents of which are incorporated herein by reference.

According to the present invention, the compound of the present invention can be used in the form monomer or composition. Further, the compound of the present invention can be administered to a patient in need of treatment via intestinal, parenteral or topical route. The intestinal route usually includes oral administration, and the form of the compound of the present invention for intestinal route use includes oral solutions, tablets, capsules, granules, and suspensions. The parenteral route usually includes subcutaneous, intramuscular, intraperitoneal, intravenous routes, etc., and the form of the compound of the present invention for parenteral route use includes injections and lyophilized preparations. The form of the compound of the present invention for topical use includes patches, pastes, ointments, etc.

Further, the disease or disorder associated with hepatitis virus is a disease or disorder associated with the late stage of hepatitis virus infection; the disease or disorder associated with hepatitis virus is a disease or disorder associated with hepatitis A virus, hepatitis B virus, or hepatitis C virus; preferably, the disease or disorder associated with hepatitis virus includes, but is not limited to: hepatitis A, hepatitis B, hepatitis C, and/or liver cirrhosis.

Further, the compound treats and/or prevents a disease or disorder associated with a hepatitis virus by modulating an immune response. Preferably, the immune response is involved in a specific T-cell response to a hepatitis virus (including, but not limited to, hepatitis A virus, hepatitis B virus, and hepatitis C virus, particularly hepatitis B virus). More preferably, the immune response is involved in the secretion of IFNγ, TNFα, IL-2 in CD4+ T cells and CD8+ T cells.

The second aspect of the present invention relates to a use of a bisdiazabicyclo compound in manufacture of a medicament for treatment and/or prevention, or elimination and/or alleviation of a disease or disorder associated with a hepatitis virus.

Further, the compound is a compound as defined above. Furthermore, the medicament includes a known drug for treatment of hepatitis virus, especially HBV, in which the drug includes, but is not limited to: IFNα-2a, Birinapant, anti-PD1 antibody, pegylated interferon α2b, pegylated interferon α2a, lamivudine, adefovir, entecavir and/or tenofovir (in particular, tenofovir disoproxil fumarate).

Further, the disease or disorder associated with a hepatitis virus is a disease or disorder associated with the late stage of hepatitis virus infection; the disease or disorder associated with hepatitis virus is a disease or disorder associated with hepatitis A virus, hepatitis B virus, or hepatitis C virus; preferably, the disease or disorder associated with hepatitis virus includes, but is not limited to: hepatitis A, hepatitis B, hepatitis C, and/or liver cirrhosis.

Further, the medicament treats and/or prevents a disease or disorder associated with a hepatitis virus by modulating an immune response. Preferably, the immune response is involved in a specific T-cell response to a hepatitis virus (including, but not limited to, hepatitis A virus, hepatitis B virus, and hepatitis C virus, particularly hepatitis B virus). More preferably, the immune response is involved in the secretion of IFNγ, TNFα, IL-2 in CD4+ T cells and CD8+ T cells.

The third aspect of the present invention relates to a method for treating and/or preventing, or eliminating and/or alleviating a disease or disorder associated with a hepatitis virus, the method comprising administering a therapeutically and/or prophylactically effective amount of the compound to a patient suffering from the disease or disorder associated with the hepatitis virus.

Further, the compound is a compound as defined above. Furthermore, the compound can be further used in combination with a known drug for treatment of hepatitis virus, especially HBV, in which the known drug for treatment of hepatitis virus, especially HBV, includes, but is not limited to: pegylated interferon α2b, pegylated interferon α2a, lamivudine, adefovir (in particular, adefovir dipivoxil), entecavir and/or tenofovir (in particular, tenofovir disoproxil fumarate).

Further, when the compound is used in combination with the drug known for treatment of hepatitis virus, especially HBV, the compound and the drug known for treatment of hepatitis virus, especially HBV, can be administered together, separately and sequentially.

Further, the disease or disorder associated with a hepatitis virus is a disease or disorder associated with the late stage of hepatitis virus infection; the disease or disorder associated with hepatitis virus is a disease or disorder associated with hepatitis A virus, hepatitis B virus, or hepatitis C virus; preferably, the disease or disorder associated with hepatitis virus includes, but is not limited to: hepatitis A, hepatitis B, hepatitis C, and/or liver cirrhosis.

Further, the compound treats and/or prevents a disease or disorder associated with a hepatitis virus by modulating an immune response. Preferably, the immune response is involved in a specific T-cell response to a hepatitis virus (including, but not limited to, hepatitis A virus, hepatitis B virus, and hepatitis C virus, particularly hepatitis B virus). More preferably, the immune response is involved in the secretion of IFNγ, TNFα, IL-2 in CD4+ T cells and CD8+ T cells.

The fourth aspect of the present invention relates to a pharmaceutical composition comprising a bisdiazabicyclo compound, the pharmaceutical composition is used for treatment and/or prevention, or elimination and/or alleviation of a disease or disorder associated with a hepatitis virus.

Further, the bisdiazabicyclo compound is a compound as defined above. Furthermore, the pharmaceutical composition can further comprise a known drug for treatment of hepatitis virus, especially HBV, in which the known drug includes, but is not limited to: interferon α2b, interferon α2a, lamivudine, adefovir (in particular, adefovir dipivoxil), entecavir and/or tenofovir (in particular, tenofovir disoproxil fumarate).

Further, the disease or disorder associated with a hepatitis virus is a disease or disorder associated with the late stage of hepatitis virus infection; the disease or disorder associated with hepatitis virus is a disease or disorder associated with hepatitis A virus, hepatitis B virus, or hepatitis C virus; preferably, the disease or disorder associated with hepatitis virus includes, but is not limited to: hepatitis A, hepatitis B, hepatitis C, and/or liver cirrhosis.

Further, the compound treats and/or prevents a disease or disorder associated with a hepatitis virus by modulating an immune response. Preferably, the immune response is involved in a specific T-cell response to a hepatitis virus (including, but not limited to, hepatitis A virus, hepatitis B virus, and hepatitis C virus, particularly hepatitis B virus). More preferably, the immune response is involved in the secretion of IFNγ, TNFα, IL-2 in CD4+ T cells and CD8+ T cells.

Specific Models for Carrying Out the Present Invention

The following examples are used to further describe the present invention, but are not intended to limit the present invention in any way.

Example 1. Effect of Single Injection of Compound 1 on HBV in C57BL/6J Mouse Model Established by High-Pressure Tail Vein Injection of pAAV-HBV1.2 Plasmid 1.1 Experimental Methods A chronic HBV infection mouse model was established using C57BL/6J mice by high-pressure tail vein injection of pAAV-HBV1.2 plasmid to simulate chronic hepatitis B patients which could obtain immune control spontaneously. Male C57/B6 mice (6-8 weeks of age, body weight 20 f 2 g) were selected to establish a high-pressure tail vein injection mouse model, in which the tail of mice was wiped with 75% alcohol, and then irradiated with a far-infrared physio-therapy device for 2 to 3 minutes so that the tail vein of mice was turgid and clearly visible. A needle was inserted in parallel along the tail vein, until feeling empty or seeing blood return, which indicated that the needle entered into the vein, and then the injection was completed within 10 s by gently pushing. Each mouse was injected with 10 µg of pAAV/HBV1.2 plasmid, and the amount of injection liquid (PBS) was 10% of body weight (2 mL/20 g). On the $14^{th}$ day after the injection, blood was collected to detect HBsAg, and the successfully modeled mice with HBsAg>500 IU/ml were selected for further experiments (Huang, Wu et al. 2006; Chou, Chien et al. 2015). After C57BL/6J mice were successfully modeled, they were divided into 4 groups: 0.9% NaCl saline injection group (Group 1 in FIGS. 1A and 1B, black lines), Compound 1 10 mg/kg intravenous injection group (Group 2 in FIGS. 1A and 1B, red lines), Compound 1 20 mg/kg intravenous injection group (Group 3 in FIGS. 1A and 1B, blue lines). There were 6-8 mice in each group, which were administered once a week for 4 consecutive times and observed for 7 weeks.

After the mice serum were diluted 20-fold with PBS, the HBsAg and HBeAg titers of the serum were detected by using Abbott i2000SR microparticle chemiluminescence automatic detector. The serum HBV DNA was extracted by QIAamp DNA Mini Kit (Qiagen), the HBV DNA level in serum was quantified by Realtime-PCR (LightCycler 480, Roche) using DNA Amplification SYBR Green Kit (Roche), and the HBV plasmid PSM2 products with a series of concentration gradients were used as standards. The HBV primers used in this experiment were synthesized by Invitrogen (Shanghai) Trading Co., Ltd., and the primer sequences were as follows: HBV Hope-F (5' to 3' TACTAG-GAGGCTGTAGGCATA) and HBV Hope-R (5' to 3' GGA-GACTCTAAGGCTTCCC). The liver tissues of mice were subjected to conventional formalin-fixation and paraffin-embedding, the resultant 4 µm sections were baked at 65° C. for 2 h, dehydrated with conventional ethanol gradients, infiltrated with hydrogen peroxide at room temperature for 30 min, washed with PBS for 5 min/time, 3 times in total, and blocked at room temperature for 1 h. After rabbit-anti-human HBcAg (B0586, DAKO) was added and incubated in a wet box at room temperature for 1 h, a GTvision III immunohistochemical detection kit of anti-rabbit anti-mice general type (GK50075, Shanghai Gene Technology Co., Ltd.) was used for incubation of secondary antibodies and development of color, and pictures at 200× magnification were taken with a normal optical upright microscope. 60 mg of liver tissue homogenate was weighed, added with 900 µl of lysate (50 mmol/L Tris-HCl PH 7.5+1 mmol/L EDTA), placed on ice, and after all samples were processed, 5 µl of NP-10 was added and lysis was performed on ice, and then HBV DNA in liver tissue was extracted with phenol/chloroform, dissolved by adding 15 µl of RNase free water, run on a 1% agarose gel, transferred to membrane; then a full-length HBV probe labeled with digoxin was added, stood overnight at 46° C., subjected to DIG Washing Buffer once for 5 min, added with Anti-Digoxigenin-Ap Fab fragment (11093274910, Roche), and Image Quant LAS 4000mini was used for exposure and detection.

Graphpad Prism 5.0 was used for mapping and relevant statistical analysis, Kruskal-Wallis H test and Dunn's Multiple Comparison test were used for multiple comparisons between groups at the same time point, log-rank Mantel-Cox test was used to compare the HBsAg and HBV DNA clearance rates in serum, * represented P<0.05,  represented p<0.01, and * represented p<0.001, in which P<0.05 indicated a statistically significant difference.

1.2 Experimental Results

As shown in FIG. 1, in comparison with the normal saline injection control group, the Compound 1 injection groups showed rapid decrease in serum HBsAg (FIG. 1A) and serum HBV DNA (FIG. 1B) after administration, and both of the serum HBsAg and HBV DNA were below the detection limit up to the $7^{th}$ week, in which the Compound 1 20 mg/kg injection group indicated that serum HBsAg and HBV DNA were completely eliminated on the $5^{th}$ week, which was faster than that of the Compound 1 10 mg/kg dose group. The liver tissue HBcAg immunohistochemical staining results showed that HBcAg expression was not observed in the liver of the mice of the Compound 1 injection groups after 7 weeks of administration, but HBcAg expression in the liver of some mice in the normal saline control group could still be detected (FIG. 1C). The results of HBV DNA Southern blot in liver tissue 7 weeks after administration showed that no HBV replication intermediate was detected in the liver tissue of the Compound 1 injection group as compared with the saline group (FIG. 1D).

The above results confirmed that four consecutive injections of Compound 1 at 20 mg/kg could completely clear HBsAg and HBV DNA in peripheral blood in the mice model infected with chronic HBV, and completely clear HBcAg expression and HBV replication intermediates in the liver on the $5^{th}$ week. These results showed that Compound 1 could completely eliminate viral antigens and nucleic acid products in a subject with chronic HBV infection. (*, p<0.05; **, p<0.01).

Example 2. Effect of Compound 1 in Combination with Tenofovir Disoproxil Fumarate (TDF) on HBV in C57BL/6J Mouse Model Established by High-Pressure Tail Vein Injection of pAAV-HBV1.2 Plasmid 2.1 Experimental Methods The C57BL/6J mouse model was established by pAAV-HBV1.2 plasmid high-pressure tail injection. C57BL/6J mice (6 to 8 weeks of age, body weight 20±2 g) were successfully modeled and divided into 4 groups, i.e., 0.9% NaCl intravenous injection group (Group 1 in FIGS. 2A and 2B, black lines), Compound 1 10 mg/kg intravenous injection group (Group 2 in FIGS. 2A and 2B, red lines), TDF 53 mg/kg gavage group (Group 3 in FIGS. 2A and 2B, blue lines), Compound 1 10 mg/kg in combination with TDF 53 mg/kg administration group (Group 4 in FIGS. 2A and 2B, purple lines). There were 6 to 8 mice in each group, Compound 1 was injected once a week for 4 consecutive times, TDF was gavaged every day for a total of 10 days, and the mice were observed for 7 weeks. Serological HBsAg and HBV DNA detection methods were the same as above.

2.2 Experimental Results

Figure 2:
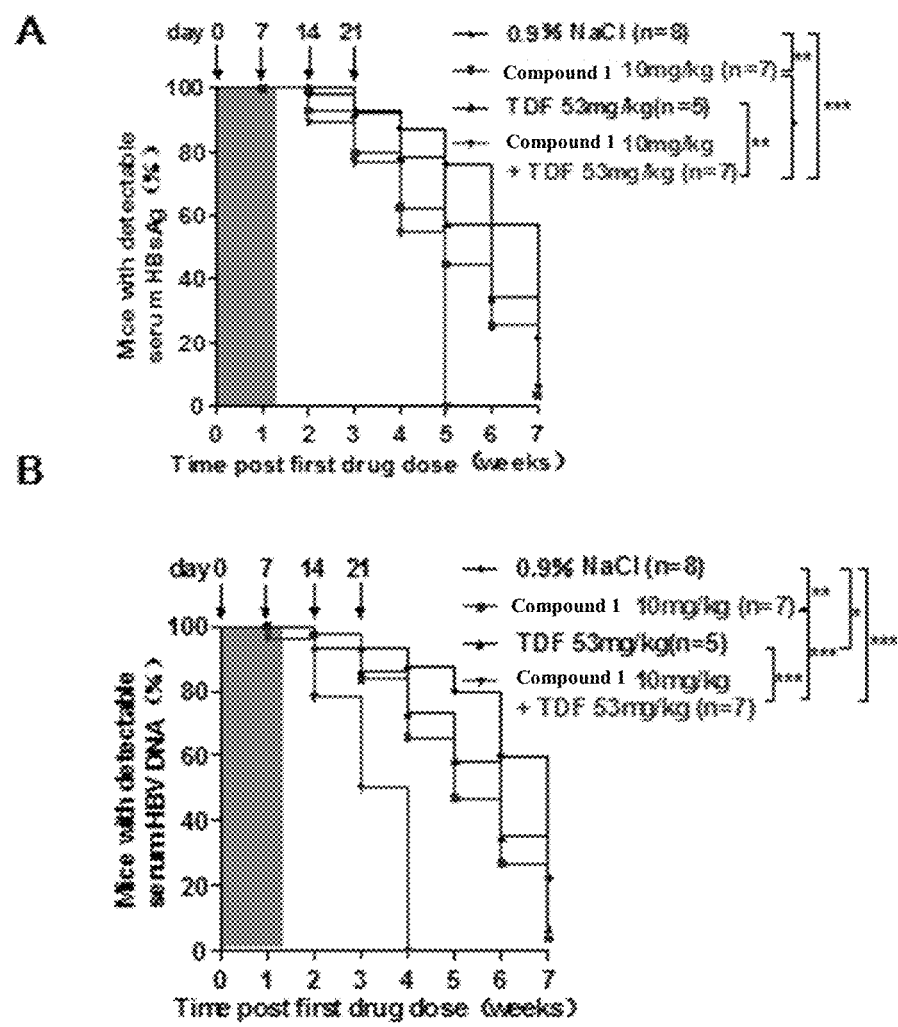
FIG. 2 shows the effect of the administration of Compound 1 in combination with tenofovir disoproxil fumarate (TDF) on HBV in a C57BL/6J mouse model established by high-pressure tail vein injection of pAAV-HBV1.2 plasmid. A: comparison of clearance rates of HBsAg in serum for different groups at different time points; B: comparison of clearance rates of HBV DNA in serum for different groups at different time points.

As shown in FIG. 2, as to serum HBsAg clearance rate (FIG. 2A), the Compound 1 single group and the Compound 1 in combination with TDF group showed statistically significant differences in serum HBsAg clearance rate in comparison with the control group, and the Compound 1 in combination with TDF group could clear HBsAg in serum faster and showed a statistically significant difference in comparison with the Compound 1 single group or the TDF single group. The above results showed that Compound 1 in combination with TDF could synergistically clear HBsAg in serum. With regard to serum HBV DNA clearance rate (FIG. 2B), the Compound 1 group, the TDF group and the Compound 1 in combination with TDF group showed statistically significant differences in comparison with the control group, and the Compound 1 in combination with TDF group could clear serum HBV DNA faster than the TDF single group or the Compound 1 single group.

The above results showed that Compound 1 in combination with TDF could accelerate the elimination of serum HBV DNA, thereby exerting a synergistic effect against virus. (*, p<0.05; , p<0.01; *, p<0.001).

Example 3. Effect of Compound 1 on Apoptosis of Liver Cells in HBV Infected Mice 3.1 Experimental Method Chronic HBV infection mouse models were established by high-pressure tail vein injection of pAAV-HBV1.2 plasmid or recombinant virus rAAV8-1.3HBV injection of C57BL/6J mice (6 to 8 weeks of age, weight 20 f 2 g). After C57BL/6J mice were successfully modeled by high-pressure tail vein injection of pAAV-HBV1.2 plasmid, the mice were injected intravenously with Compound 1 at 10 mg/kg, and serum and liver tissues of the mice were collected at 12, 24, and 48 hours after injection. Glutamic-oxalacetic transaminase (AST/GOT) kit (Nanjing Jiancheng, C010-2) and glutamic-pyruvic transaminase (ALT/GPT) kit (Nanjing Jiancheng, C009-2) were used to detect serum ALT and AST levels. Western blot was used to detect the expression of cIAPs molecules in liver tissues, and β-actin was used as a control. Intrahepatic inflammation and hepatocyte necrosis were detected by HE staining of liver tissue sections. C57BL/6J mice were subjected to conventional tail vein injection of rAAV8-1.3HBV (ayw) virus at viral injection amount of $5 \times 10^5$ v.g./mice (Yang, Liu et al. 2014) to establish the rAAV8-HBV1.3 virus injection C57BL/6J mouse model; the mice were sacrificed 12 hours after the intravenous injection of Compound 1 at 20 mg/kg, and the HBV-infected hepatocyte apoptosis was subjected to double staining detection of HBcAg immunofluorescence and Tunnel method.

3.2 Experimental Results

Figure 3:
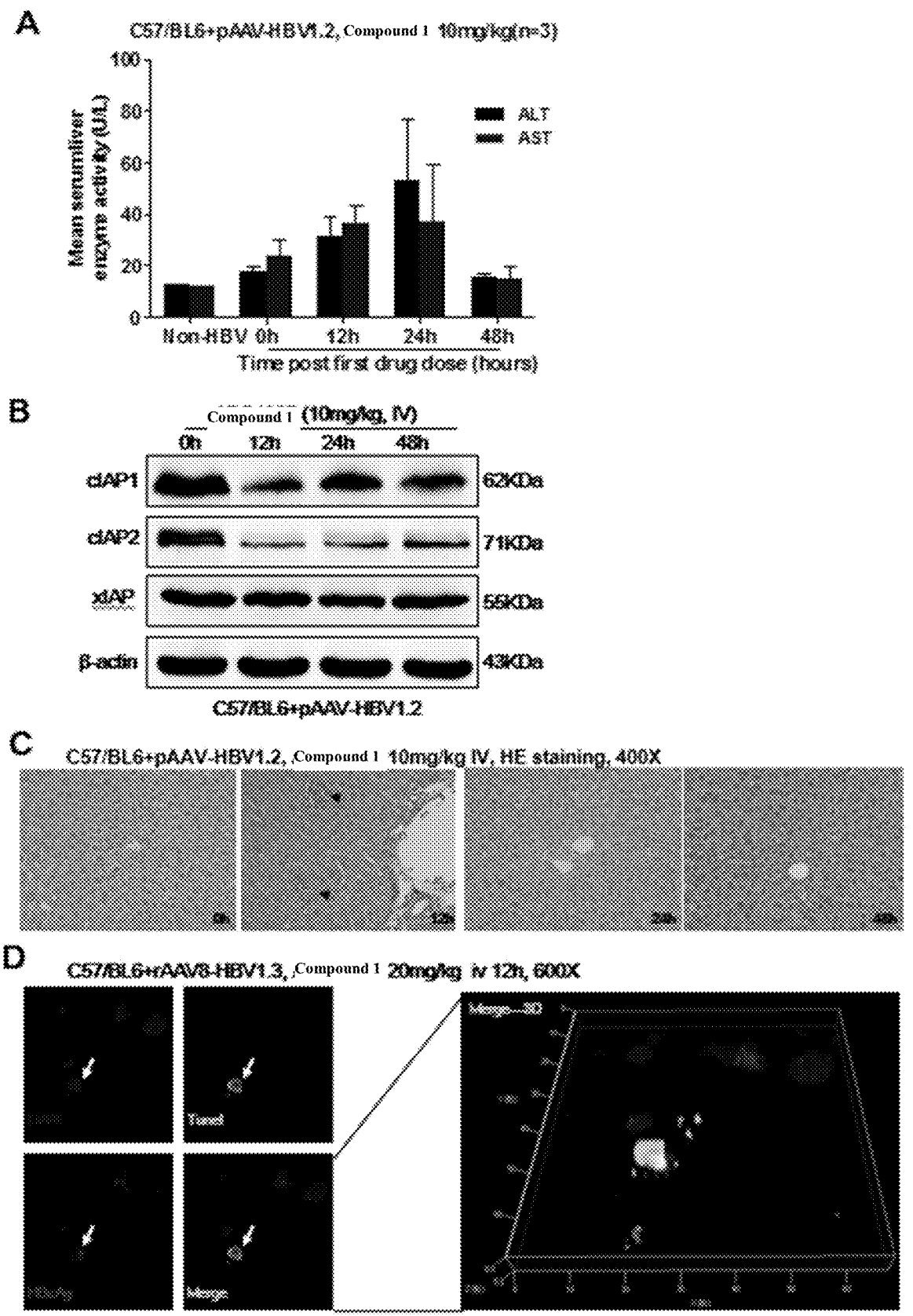
FIG. 3 shows the effect of Compound 1 on hepatocyte apoptosis in HBV-infected mice. A: dynamic changes of ALT and AST in serum at different time points after Compound 1 injection for the C57BL/6J mice subjected to high-pressure tail vein injection of pAAV-HBV1.2 plasmid; B: expression changes of cIAPs in liver tissue at different time points after Compound 1 injection: C: HE staining of liver tissue sections of mice at different time points after Compound 1 injection; D: apoptosis of HBV-infected liver cells detected by HBcAg immunofluorescence and Tunnel double staining method.

As shown in FIG. 3, after injection of Compound 1, the serum transaminases ALT and AST, which reflected liver cell damage, showed a transient increase, i.e., they rose to the highest values at 12 hours, then slowly decreased, and returned to normal levels around 48 hours (FIG. 3A). The detection of IAPs molecules in the liver by Western blot revealed that Compound 1 had strong inhibitory effect on cIAP2 in liver tissues, which reached the strongest value at 12 h; it also had an inhibitory effect on cIAP1, but was significantly weaker than that on cIAP2; while no significant inhibitory effect was observed on XIAP (FIG. 3B). The liver tissue HE staining also showed that 12 hours after the injection, scattered necrotic lesions appeared in the vicinity of the portal areas in the liver tissue, accompanied by lymphocyte infiltration (FIG. 3C). The double staining experiment of Tunel staining and HBcAg fluorescence was used to observe the apoptosis of HBV-infected liver cells, and in combination with double-staining 3D picture analysis, it was found that 12 h after injection of Compound 1, the apoptosis of HBcAg-positive liver cells could be induced (FIG. 3D).

The above results suggested that Compound 1 could specifically induce the apoptosis of HBV-infected liver cells and contribute to the clearance of virus; in addition, it only induced transient intrahepatic inflammation and did not cause fulminant hepatitis, thereby reducing adverse reactions possibly caused by the treatment.

Example 4. Effect of Compound 1 on HBV Immune Response in Mice 4.1 Experimental Methods C57BL/6J mice (6-8 W week old, weight 20±2 g) were subjected to high-pressure tail vein injection of pAAV-HBV1.2 plasmid to establish a chronic HBV infection mouse model. After the modeling was successful, the mice were divided into two groups: Group A: 0.9% NaCl biological saline injection group; Group B: Compound 1 20 mg/kg injection group. There were 5 to 6 mice in each group, which were administered once a week for four consecutive times, and sacrificed on the $7^{th}$ week, the mice liver lymphocytes were isolated, and cell counts and flow cytometry were used to detect the expression of CD4 and CD8 molecules in lymphocytes in the liver. The detection of HBV-specific T cell response was performed by using HBV core monopeptide (Core93-100) to stimulate lymphocytes, and the counts of CD4+ and CD8+ T cells that secreted IFNγ, TNFα and IL-2 were detected by flow cytometry cytokine intracellular staining method.

4.2 Experimental Results

Figure 4:
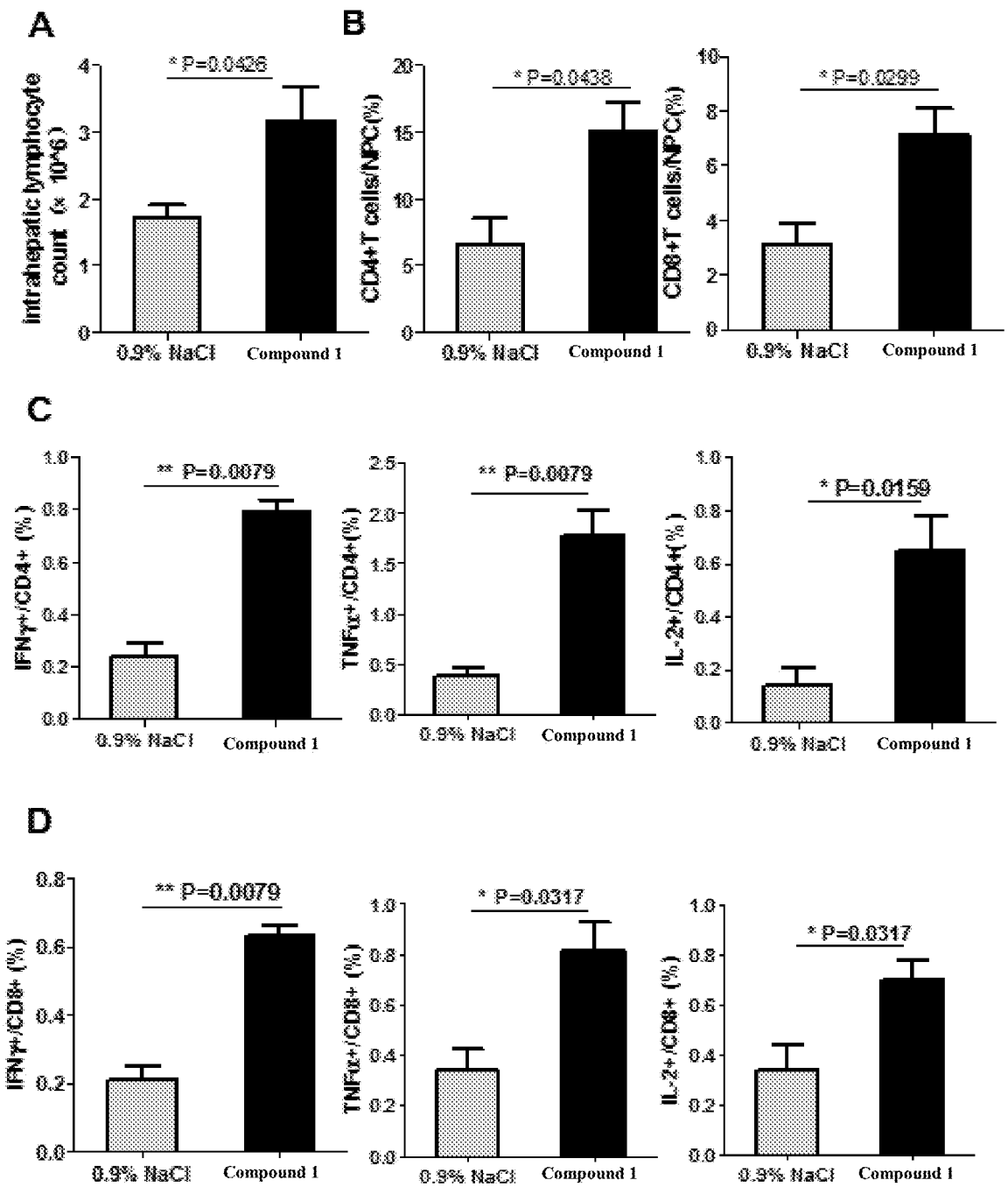
FIG. 4 shows the influential effect of Compound 1 treatment on HBV immune response in mice. A: changes of total lymphocyte count in liver after the viruses were cleared from the liver of the mice in the Compound 1 treatment group; B: changes of counts of infiltrated CD4+ T cells and CD8+ T cells in liver; C: function of HBV-specific CD4+ T cells in term of secretion of IFNγ, TNFα, IL-2; D: function of HBV-specific CD8+ T cells in term of secretion of IFNγ, TNFα, IL-2.

As shown in FIG. 4, after the virus was cleared from the liver of the mice in the Compound 1 treatment group, the total lymphocyte number in the liver was significantly higher than that in the normal saline control group (FIG. 4A). Further analysis revealed that compared with the control, the counts of infiltrated CD4+ T cells and CD8+ T cells in the liver were significantly increased (FIG. 4B). After stimulation with HBV core monopeptide (Core93-100), the counts of CD4+ T cells that secreted IFNγ, TNFα and IL-2 increased significantly (FIG. 4C), and the counts of CD8+ T cells that secreted IFNγ, TNFα and IL-2 increased significantly (FIG. 4D).

The above results showed that after treatment with Compound 1 and clearance of virus, the specific T cell response function against HBV in the liver was significantly enhanced, which was conducive to the clearance of virus. Further, Compound 1 could specifically induce the apoptosis of HBV-infected hepatocytes by up-regulating HBV-specific T cell responses, thereby eliminating viral antigens and other viral products.

Example 5. Anti-HBV Effect of the Administration of Compound 1 in Combination with IFNα2a in Chronic HBV Infection C57BL/6J Mouse Model 5.1 Experimental Methods Chronic HBV infection mouse model was established using C57BL/6J mice (6 to 8 W, body weight 20 t 2 g) that were subjected to the high-pressure tail vein injection of a mixture of pAAV-HBV1.2 plasmid and pKCMvint IFNα-2a plasmid or pKCMvint control plasmid (6 μg/mouse), and expressed IFNα2a. One day after modeling, the mice were divided into 4 groups. Group A (0.9% saline injection group): pAAV-HBV1.2+pKCMvint+0.9%/NaCl; Group B (Compound 1 10 mg/kg intravenous injection group): pAAV-HBV1.2+pKCMvint+Compound 1 10 mg/kg; Group C (IFNα-2a group): pAAV-HBV1.2+pKCMvint IFNα-2a+ 0.9% NaCl; Group D (Compound 1 in combination with IFNα-2a group): pAAV-HBV1.2+pKCMvint IFNα-2a+ APG 10 mg/kg. There were 5 mice in each group (except Group D that included 7 mice), the administration was performed for consecutive 3 times, i.e., on the day 1 after modeling, and on the days 7 and 14 after modeling; blood was collected once at orbital margin one day before the administration, and serum HBsAg/HBeAg levels were detected using Roche 601 instrument.

5.2 Experimental Results

Figure 5A:
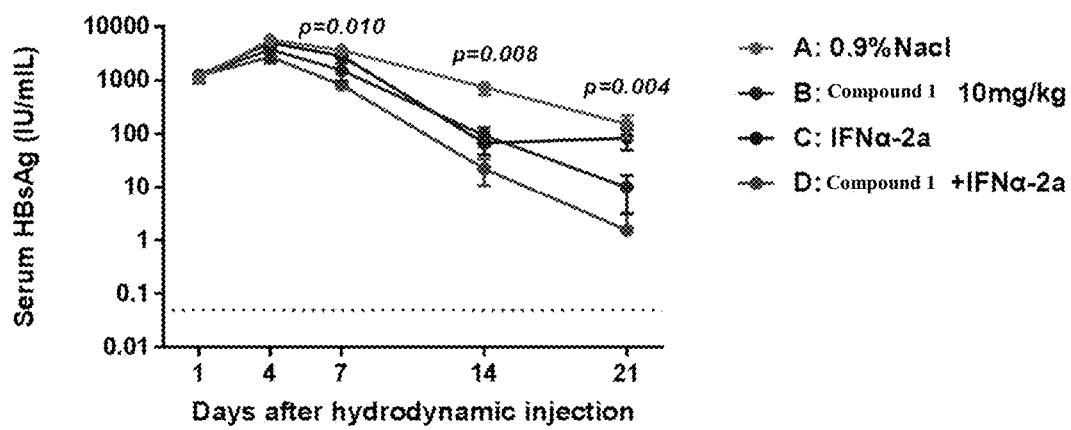
FIG. 5A: changes of individual serum HBsAg level at different time points within 21 days after the first administration for each group (Group A (0.9% saline injection group): pAAV-HBV1.2+pKCMvint+0.9% NaCl; Group B (Compound 1 10 mg/kg intravenous injection group): pAAV-HBV1.2+pKCMvint+Compound 1 10 mg/kg; Group C (IFNα-2a group): pAAV-HBV1.2+pKCMvint IFNα-2a+0.9% NaCl; Group D (Compound 1 in combination with IFNα-2a group): pAAV-HBV1.2+pKCMvint IFNα-2a+APG 10 mg/kg).
Figure 5B:
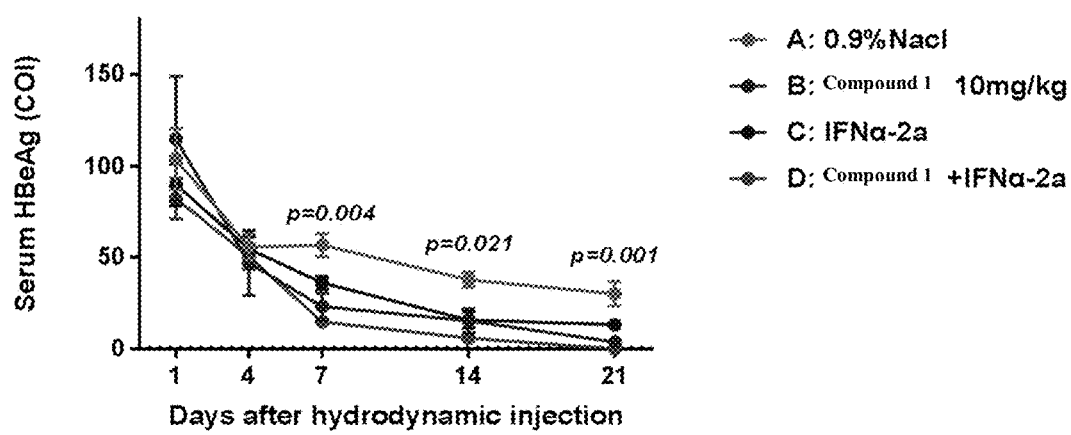
FIG. 5B: changes of individual serum HBeAg level at different time points within 21 days after the first administration for each group (Group A (0.9% saline injection group): pAAV-HBV1.2+pKCMvint+0.9% NaCl; Group B (Compound 1 10 mg/kg intravenous injection group): pAAV-HBV1.2+pKCMvint+Compound 1 10 mg/kg; Group C (IFNα-2a group): pAAV-HBV1.2+pKCMvint IFNα-2a+0.9% NaCl; Group D (Compound 1 in combination with IFNα-2a group): pAAV-HBV1.2+pKCMvint IFNα-2a+APG 10 mg/kg).

As shown in FIGS. 5A and 5B, the serum HBsAg and HBeAg levels were statistically different between different treatment groups on the $7^{th}$, $14^{th}$, and $21^{st}$ days after modeling. As shown in FIG. 5A, as compared Group B, Group C and Group D with Group A, the former 3 groups showed statistically significant differences in serum HBsAg on the $7^{th}$, $14^{th}$, and $21^{st}$ days, that was, the P value was 0.010 on the $7^{th}$ day, the P value was 0.008 on the $14^{th}$ day, and the P value was 0.004 on the $21^{st}$ day, in which a statistical difference between the groups was determined when P value was less than 0.05, and wherein the decrease of serum HBsAg in the combined treatment Group D was the most significant. On the $21^{st}$ day, compared with Group C, the serums of Group B and Group D decreased significantly, and their P values were both 0.008, that was, the P value of Group C compared to Group B was 0.008, and the P value of Group C compared to Group D was 0.008 (the P values of separate comparisons for the both were not shown in the figures). As shown in FIG. 5B, as compared Group B, Group C and Group D with Group A, the former 3 groups showed statistically significant differences in serum HBeAg on the $7^{th}$, $14^{th}$, and $21^{st}$ days, that was, the P value was 0.004 on the $7^{th}$ day, the P value was 0.021 on the $7^{th}$ day, and the P value was 0.001 on the $21^{st}$ day, in which a statistical difference between the groups was determined when P value was less than 0.05, and wherein, the decrease of HBeAg in the combined treatment group D was the most significant. On the $21^{st}$ day, compared with Group C and Group B, the serum of Group D was significantly decreased, and the P values were both 0.008, that was, the P value of Group D compared to Group B was 0.008, and the P value of Group D compared to Group C was 0.008 (the P values of separate comparisons for the both were not shown in the figures).

The above results showed that the Compound 1 in combination with IFNα2a group had the most significant effect in reducing HBsAg/HBeAg. Therefore, the Compound 1 in combination with IFNα2a group had anti-HBV effect in the chronic HBV infection mouse model established in C57BL/6J mice by high-pressure tail vein injection of the mixture of pAAV-HBV1.2 plasmid and pKCMvint IFNα-2a plasmid or pKCMvint control plasmid.

Example 6. Comparison of Anti-HBV Effect of Compound 1 and Birinapant in Chronic HBV Infection C57BL/6J Mouse Model Established by High-Pressure Tail Vein Injection of pAAV-HBV1.2 Plasmid 6.1 Experimental Method C57BL/6J mice (6 to 8 weeks of age, weight 20+2 g) were subjected to high-pressure tail vein injection of pAAV-HBV1.2 plasmid to establish a chronic HBV infection mouse model. After successful modeling, the mice were divided into 3 groups: Group A: 0.9% NaCl saline injection group; Group B: Compound 1 20 mg/kg intravenous injection group, and Group C: Birinapant 20 mg/kg intravenous injection group. Among them, there were 7 mice in each of Group A and Group B, and 6 mice in Group C. Compound 1 and Birinapant were administered once a week for five consecutive weeks. Blood was collected at orbital margin each week before the administration, and the HBsAg/HBeAg levels in supernatant were detected using Roche 601 instrument.

6.2 Experimental Results

Figure 6A:
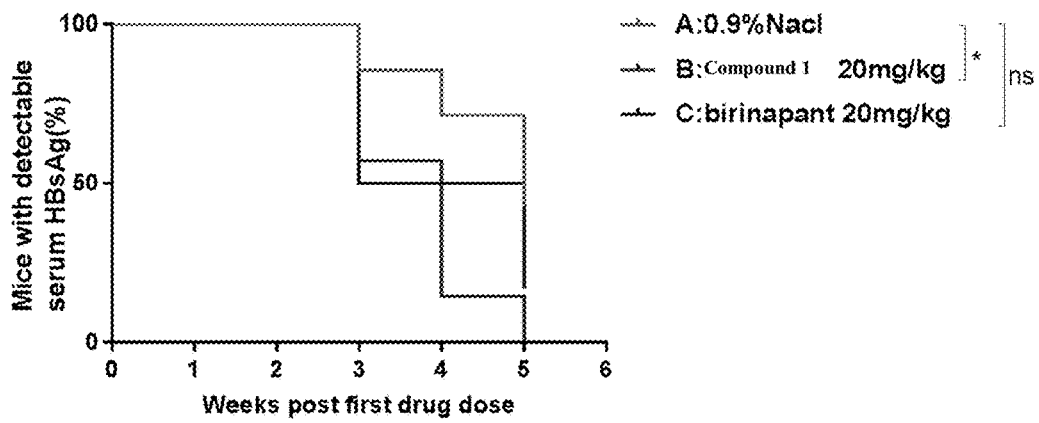
FIG. 6A: changes of overall serum HBsAg level at different time points within five weeks after the first administration for each group (Group A: 0.9% NaCl saline injection group; Group B: Compound 1 20 mg/kg intravenous injection group; Group C: Birinapant 20 mg/kg intravenous injection group)
Figure 6B:
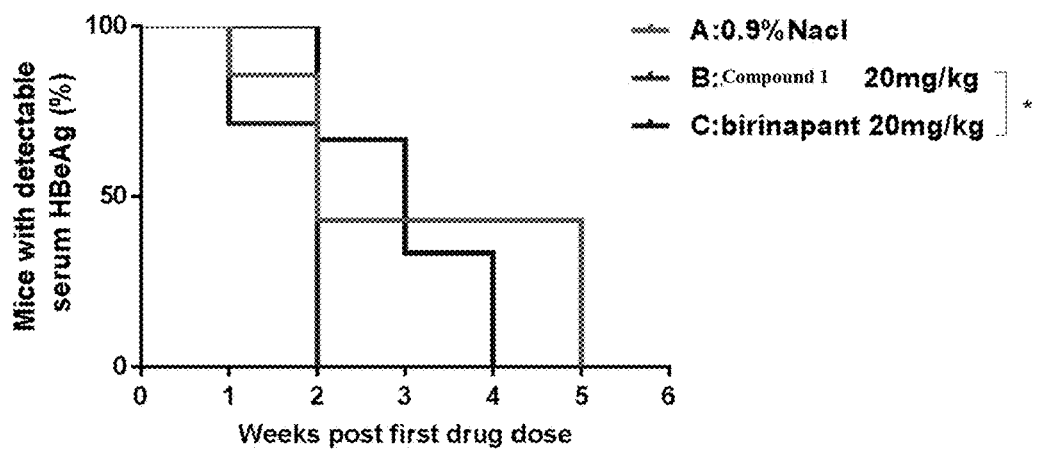
FIG. 6B: changes of overall serum HBeAg level at different time points within five weeks after the first administration for each group (Group A: 0.9% NaCl saline injection group; Group B: Compound 1 20 mg/kg intravenous injection group; Group C: Birinapant 20 mg/kg intravenous injection group)

From the changes in the overall levels of HBsAg and HBeAg in plasma, as shown in FIG. 6A, as to the clearance effect of HBsAg, there was a statistically significant difference between the Compound 1 intravenous injection group and the saline injection group. As shown in FIG. 6B, with regard to the clearance effect of HBeAg, there was a statistically significant difference between the Compound 1 intravenous group and the Birinapant group (*, p<0.05).

Figure 6C:
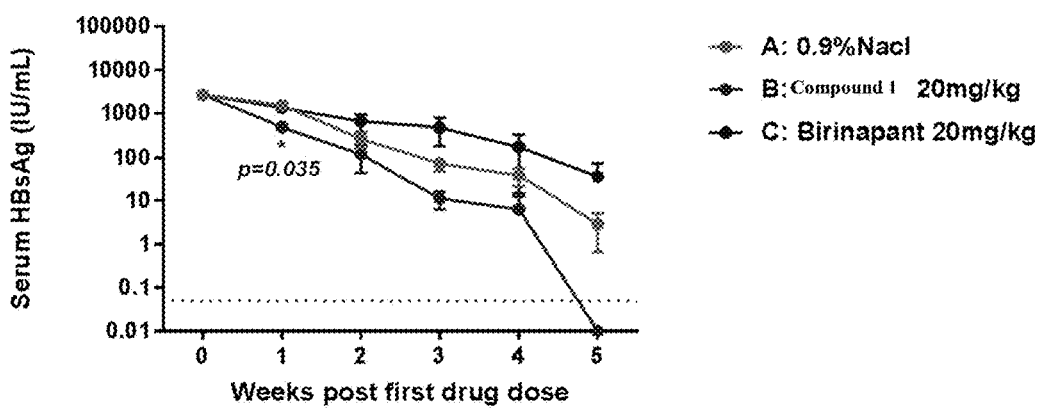
FIG. 6C: changes of individual serum HBsAg level at different time points within five weeks after the first administration for each group (Group A: 0.9% NaCl saline injection group; Group B: Compound 1 20 mg/kg intravenous injection group; Group C: Birinapant 20 mg/kg intravenous injection group)
Figure 6D:
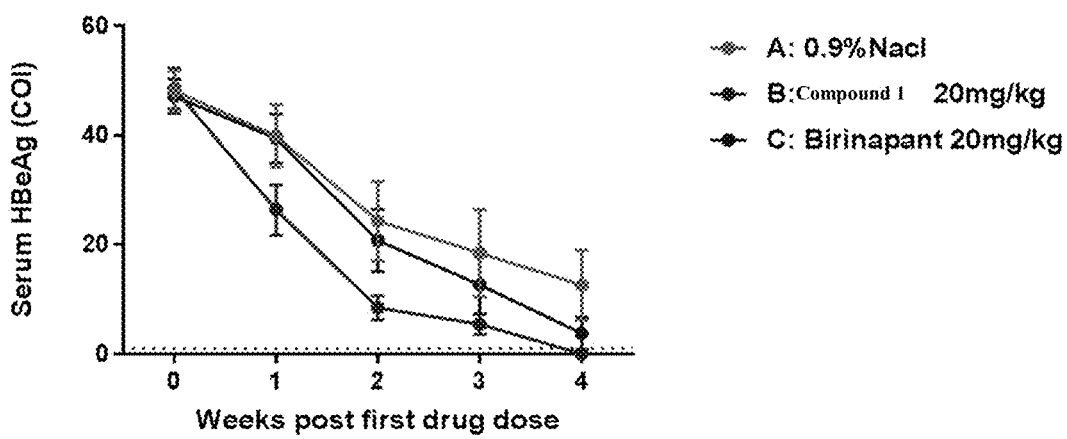
FIG. 6D: changes of individual serum HBeAg level at different time points within four weeks after the first administration for each group (Group A: 0.9% NaCl saline injection group; Group B: Compound 1 20 mg/kg intravenous injection group; Group C: Birinapant 20 mg/kg intravenous injection group).

From the change of individual levels of HBsAg and HBeAg in plasma, as shown in FIG. 6C, after one week of drug treatment, the serum HBsAg levels of the both drug treatment groups decreased significantly, and the serum HBsAg level of the Compound 1 group was significantly lower than that of the Brinapant group (p=0.035).

After 4 weeks of administration, 86% of the mice in the Compound 1 group had serum HBsAg levels below the lower limit of detection, while the corresponding proportion of the Brinapant group was 57%, and this value had been illustrated in FIG. 6A (data were not shown).

The above results indicated that Compound 1 was superior to Birinapant in terms of the clearance effect of HBsAg and HBeAg. Therefore, in the same dosage and mode of administration, the antiviral effect of Compound 1 was superior to that of Birinapant.

Example 7. Anti-HBV Effect of the Administration of Compound 1 in Combination with Anti-PD1 Antibody in Chronic HBV Infection C57BL/6J Mouse Model Established by High-Pressure Tail Vein Injection of pAAV-HBV1.2 Plasmid 7.1 Experimental Methods C57BL/6J mice (6-8 weeks of age, weight 20 t 2 g) were subjected to high-pressure tail vein injection of pAAV-HBV1.2 plasmid to establish a chronic HBV infection mouse model. After the modeling was successful, the mice were divided into 4 groups: Group A: 0.9% NaCl saline injection group; Group B: Compound 1 20 mg/kg intravenous injection group; Group C: anti-PD1 antibody 200 μg/mice/time peritoneal injection group; Group D: Compound 1 in combination with anti-PD1 antibody group. Among them, there were 7 mice in each group. Compound 1 was administered intravenously once per week, and anti-PD1 antibody was administered intraperitoneally twice per week. Blood was collected from the orbital margin before the administration of Compound 1 every week, and the HBsAg/HBeAg levels in the supernatant were detected using a Roche 601 instrument.

7.2 Experimental Results

Figure 7A:
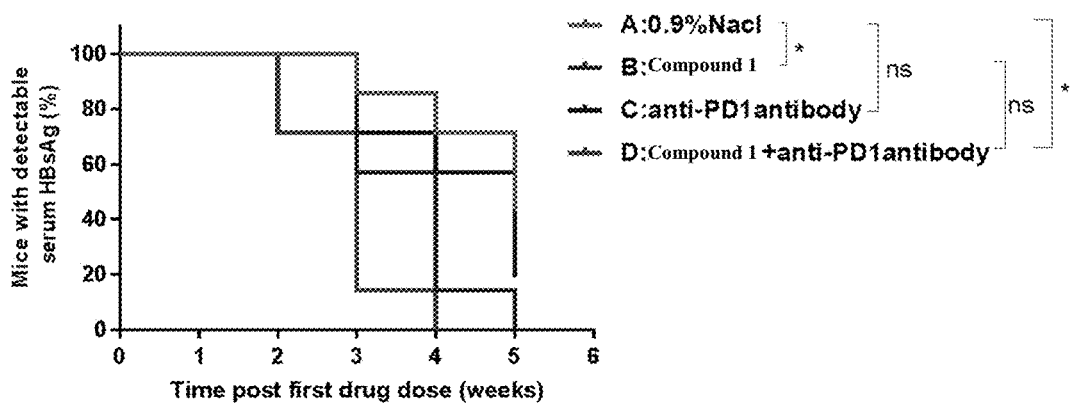
FIG. 7A: changes of overall serum HBsAg level at different time points within five weeks after first administration for each group (Group A: 0.9% NaCl saline injection group; Group B: Compound 1 20 mg/kg intravenous injection group; Group C: anti-PD1 antibody intraperitoneal injection group; Group D: Compound 1 in combination with anti-PD1 antibody group)
Figure 7B:
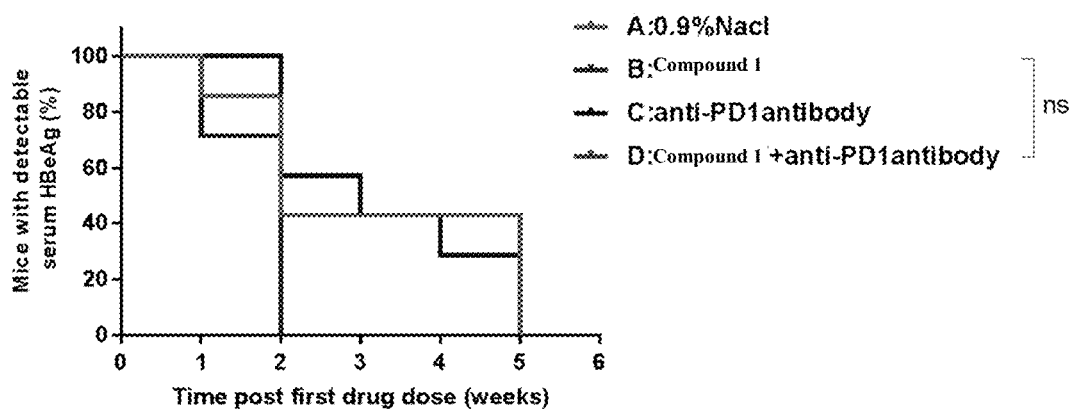
FIG. 7B: changes of overall serum HBeAg level at different time points within five weeks after first administration for each group (Group A: 0.9% NaCl saline injection group; Group B: Compound 1 20 mg/kg intravenous injection group; Group C: anti-PD1 antibody intraperitoneal injection group; Group D: Compound 1 in combination with anti-PD1 antibody group)

From the changes in overall levels of HBsAg and HBeAg in plasma, as shown in FIGS. 7A and 7B, the Compound 1 single group and the Compound 1 in combination with anti-PD1 antibody administration group could significantly reduce serum HBsAg/HBeAg levels. The anti-PD1 antibody single group showed no significant decrease in the HBsAg/HBeAg effect.

Figure 7C:
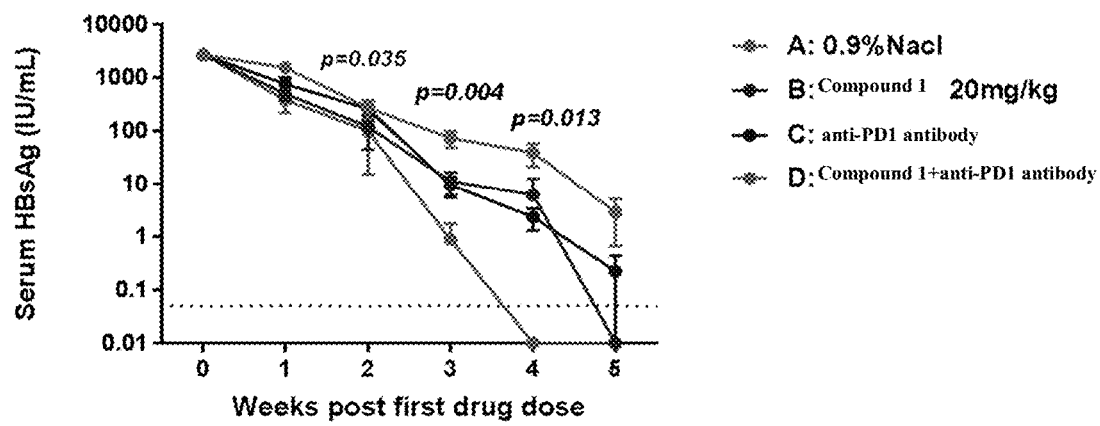
FIG. 7C: changes of individual serum HBsAg level at different time points within five weeks after first administration for each group (Group A: 0.9% NaCl saline injection group; Group B: Compound 1 20 mg/kg intravenous injection group; Group C: anti-PD1 antibody intraperitoneal injection group; Group D: Compound 1 in combination with anti-PD1 antibody group)
Figure 7D:
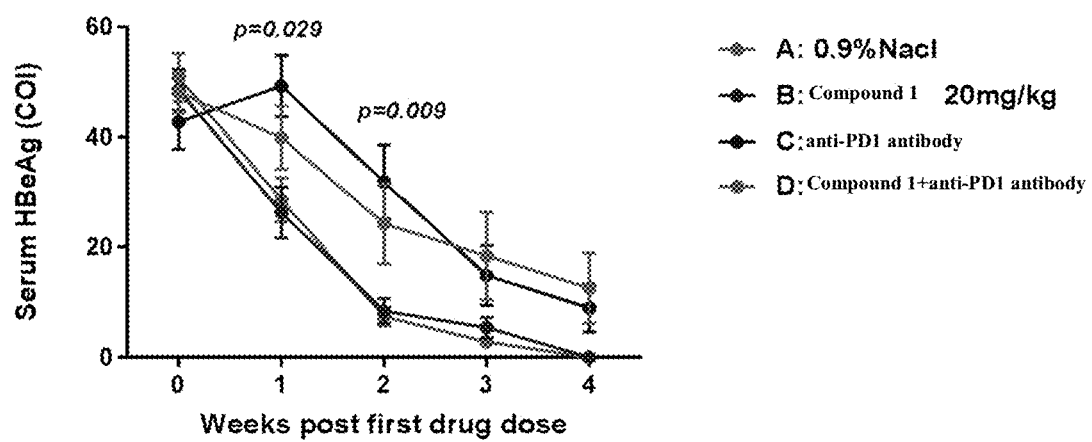
FIG. 7D: changes of individual serum HBeAg level at different time points within four weeks after first administration for each group (Group A: 0.9% NaCl saline injection group; Group B: Compound 1 20 mg/kg intravenous injection group; Group C: anti-PD1 antibody intraperitoneal injection group; Group D: Compound 1 in combination with anti-PD1 antibody group).

From the changes in individual levels of HBsAg and HBeAg in plasma, as shown in FIG. 7C, as compared Group B, Group C and Group D with Group A, the 3 groups of different drugs showed statistically significant differences in serum HBsAg on the $2^{nd}$, $3^{rd}$ and $4^{th}$ weeks, that was, the P value was 0.035 on the $2^{nd}$ week, the P value was 0.005 on the $3^{rd}$ week, and the P value was 0.013 on the $4^{th}$ week, in which a statistical difference between the groups was determined when P value was less than 0.05, and wherein the decrease of serum HBsAg in the combined treatment Group D was the most significant. As compared with Group C, the serum HBsAg of Group D decreased more significantly on the $2^{nd}$ and $3^{rd}$ weeks after administration, and the P values were 0.015 and 0.037, respectively (the P values of separate comparisons for the both in the weeks 2 and 3 were not shown in the figures). As shown in FIG. 7D, as compared Group B, Group C and Group D with Group A, the 3 groups of different drugs showed statistically significant differences in serum HBeAg on the $1^{st}$ and $2^{nd}$ weeks, that was, the P value was 0.029 on the $1^{st}$ week, the P value was 0.009 on the $2^{nd}$ week, and a statistical difference between the groups was determined when P value was less than 0.05. As compared with Group C, the serum HBeAg levels of Group B and Group D decreased more significantly on the $1^{st}$ and $2^{nd}$ weeks after administration, the P values on the $1^{st}$ week were 0.016 and 0.007 respectively, and the P values on the $2^{nd}$ week were 0.007 and 0.002 respectively (the P values of separate comparisons for the both on the $1^{st}$ and $2^{nd}$ weeks were not shown in the figures), but there was no statistical difference between Group B and Group D.

The above results showed that Compound 1 and Compound 1 in combination with anti-PD1 antibody had anti-HBV effect in the chronic HBV infection C57BL/6J mouse model established by high-pressure tail vein injection of pAAV-HBV1.2 plasmid.

Example 8. Anti-HBV Effect of Compound 1 and SF18 in C57BL/6J Mouse Model Established by rAAV8-HBV1.3 (Ayw) Virus Tail Vein Injection 8.1 Experimental Methods C57BL/6J mice were subjected to conventional tail vein injection of rAAV8-HBV1.3 (ayw) virus, the injection volume of virus was $5 \times 10^5$ vg/mouse (Yang, Liu et al. 2014), and thus rAAV8-HBV1.3 virus injection C57BL/6J mouse model was established. After successful modeling, the mice were divided into three groups: Group A: 0.9% NaCl saline injection group; Group B: Compound 1 20 mg/kg intravenous injection group, and Group C: SF18 20 mg/kg intravenous injection group. Among them, there were 3 mice in each group. Administration was carried out for consecutive four weeks, blood was collected at orbital margin once per week, and HBsAg/HBeAg levels in supernatant were detected by Roche 601 instrument.

8.2 Experimental Results

Figure 8A:
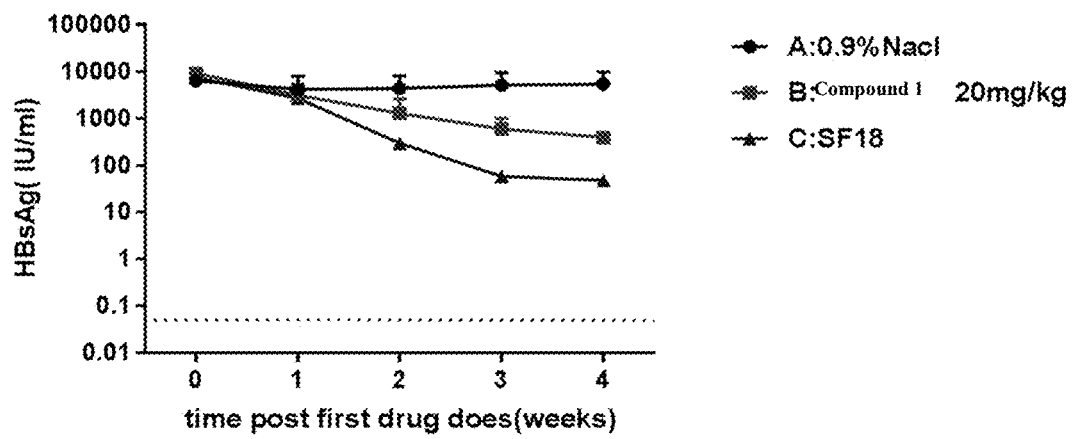
FIG. 8A: changes of individual HBsAg level at different time points within four weeks after first administration for each group (Group A: 0.9% NaCl saline injection group; Group B: Compound 1 20 mg/kg intravenous injection group; Group C: SF18 20 mg/kg intravenous injection Group)
Figure 8B:
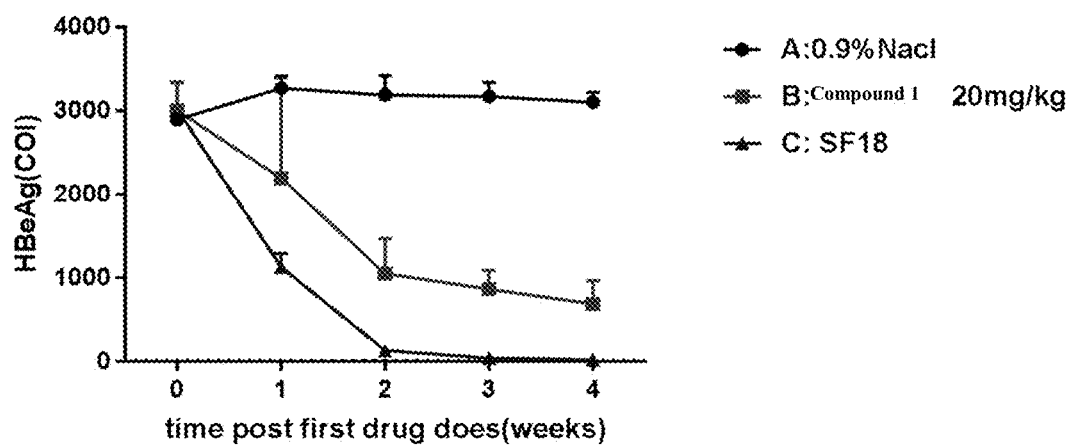
FIG. 8B: changes of individual HBeAg level at different time points within four weeks after first administration for each group (Group A: 0.9% NaCl saline injection group; Group B: Compound 1 20 mg/kg intravenous injection group; Group C: SF18 20 mg/kg intravenous injection Group).

As shown in FIGS. 8A and 8B, the decrease rates of HBsAg/HBeAg in mice serum of the SF18 group were significantly faster than those of the Compound 1 group, but one mice died on the $2^{nd}$ week and $4^{th}$ week of SF18 administration, respectively.

The above results showed that both Compound 1 and SF18 had anti-HBV effect, and the anti-HBV effect of SF18 was stronger than that of Compound 1.

REFERENCES

Bertoletti, A. and C. Ferrari (2012). "Innate and adaptive immune responses in chronic hepatitis B virus infections: towards restoration of immune control of viral infection." *Gut* 61 (12): 1754-1764.

Chou, H H, W H Chien, L Wu, C H Cheng, C H Chung, J H Homg, Y H Ni, H T Tseng, D. Wu, X. Lu, H Y Wang, P J Chen and D S Chen (2015). "Age-related immune clearance of hepatitis B virus infection requires the establishment of gut microbiota." *Proc Natl Acad Sci USA* 112 (7): 2175-2180.

European Association For The Study Of The, L. (2012). "EASL clinical practice guidelines: Management of chronic hepatitis B virus infection." *J Hetol* 57 (1): 167-185.

Gish, R G, B D Given, C.-L. Lai, S A Locarnini, J Y N Lau, D L Lewis and T. 0 (2015). "Chronic hepatitis B: Virology, natural history, current management and a glimpse at future opportunities." *Antiviral Research* 121: 47-58.

Guidotti, L G, D. Inverso, L. Sironi, P. Di Lucia, J. Fioravanti, L. Ganzer, A. Fiocchi, M. Vacca, R. Aiolfi, S. Sammicheli, M. Mainetti, T. Cataudella, A. Raimondi, G. Gonzalez-Aseguinolaza, U. Protzer, Z M Ruggeri, F V Chisari, M. Isogawa, G. Sitia and M. Iannacone (2015). "Immunosurveillance of the liver by intravascular effector CD8 (+) T cells." *Cell* 161 (3): 486-500.

Guidotti, L. G., R. Rochford, J. Chung, M. Shapiro, R. Purcell and F. V. Chisari (1999). "Viral clearance without destruction of infected cells during acute HBV infection." *Science* 284 (5415): 825-829.

Hoh, A., M. Heeg, Y. Ni, A. Schuch, B. Binder, N. Hennecke, H E Blum, M. Nassal, U. Protzer, M. Hofmann, S. Urban and R. Thimme (2015) "Hepatitis B Virus-Infected HepG2hNTCP Cells Serve as a Novel Immunological Tool To Analyze the Antiviral Efficacy of CD8+ T Cells In Vitro." *J Virol* 89 (14): 7433-7438.

Huang, L. R., H. L. Wu, P. J. Chen and D. S. Chen (2006). "An immunocompetent mouse model for the tolerance of human chronic hepatitis B virus infection." *Proc Natl Acad Sci USA* 103 (47): 17862-17867.

Liaw, Y F, N. Leung, J H Kao, T. Piratvisuth, E. Gane, K H Han, R. Guan, G K Lau, S. Locamini and BGWP ot A.-PA ft S. ot L. Chronic Hepatitis (2008) "Asian-Pacific consensus statement on the management of chronic hepatitis B: a 2008 update." Hepato Int. 2 (3): 263-283.

Liu, J., H I Yang, M H Lee, S N Lu, C L Jen, R. Batrla-Utermann, L Y Wang, S L You, C K Hsiao, P J Chen, C J Chen and REVEALHS Group (2014). "Spontaneous seroclearance of hepatitis B seromarkers and subsequent risk of hepatocellular carcinoma." *Gut* 63 (10): 1648-1657.

Lok, A. S. and B. J. McMahon (2009). "Chronic hepatitis B: update 2009." *Hepatology* 50 (3): 661-662.

Lucifora, J. and C. Trepo (2015). "Hepatitis: After HCV cure, HBV cure?" *Nat Rev Gastroenterol Hepatol* 12 (7): 376-378.

Lucifora, J., Y. Xia, F. Reisinger, K. Zhang, D. Stadler, X. Cheng, M F Sprinzl, H. Koppensteiner, Z. Makowska, T. Volz, C. Remouchamps, W M Chou, W E Thasler, N. Huser, D. Durantel, T J Liang, C. Munk, M H Heim, J L Browning, E. Dejardin, M. Dandri, M. Schindler, M. Heikenwalder and U. Protzer (2014). "Specific and nonhepatotoxic degradation of nuclear hepatitis B virus cccDNA." *Science* 343 (6176): 1221-1228.

Nassal, M. (2015). "HBV cccDNA: viral persistence reservoir and key obstacle for a cure of chronic hepatitis B." *Gut* 64 (12): 1972-1984.

Sundaram, V. and K. Kowdley (2015). "Management of chronic hepatitis B infection." *BMJ* 351: h4263.

Wong, D. K., W. K. Seto, J. Fung, P. Ip, F. Y. Huang, C. L. Lai and M. F. Yuen (2013). "Reduction of hepatitis B surface antigen and covalently closed circular DNA by nucleos(t)ide analogues of different potency." *Clin Gastroenterol Hepatol* 11(8): 1004-1010 e1001.

Yang, D., L. Liu, D. Zhu, H. Peng, L. Su, Y. X. Fu and L. Zhang (2014). "A mouse model for HBV immunotolerance and immunotherapy." *Cell Mol Immunol* 11(1): 71-78.

What is claimed is:

1. A method of using a compound for treatment of a disease or disorder associated with a hepatitis virus, wherein the method comprises administering a therapeutically effective amount of the compound to a patient having the disease or disorder associated with a hepatitis virus, and the compound is a bisdiazabicyclo compound or a pharmaceutically acceptable salt thereof, wherein the disease or disorder associated with hepatitis virus is hepatitis A, hepatitis B, hepatitis C, or liver cirrhosis, and the compound is

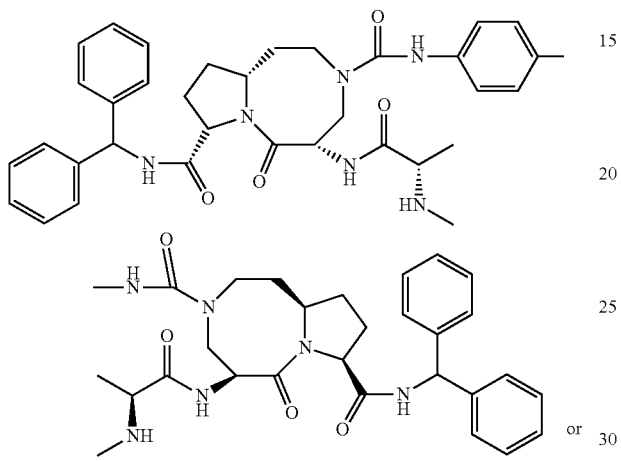

or

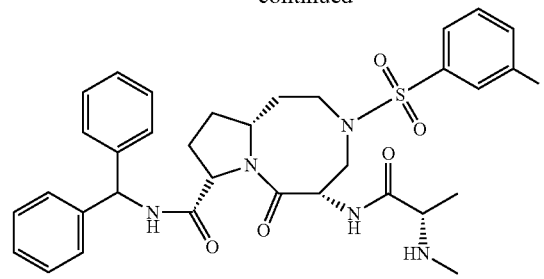

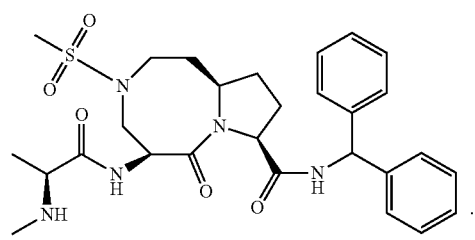

2. The method according to claim 1, wherein the compound is

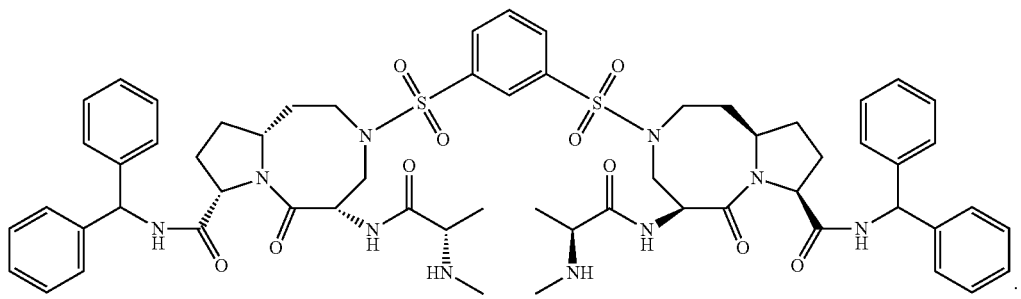

3. The method according to claim 1, wherein the compound treats the disease or disorder associated with hepatitis virus by modulating an immune response.

4. The method according to claim 1, wherein the method comprises using the compound in combination with a drug known to treat HBV.

5. A method of treating a patient having hepatitis B, comprising administering to the patient a therapeutically effective amount of a compound, wherein the compound is

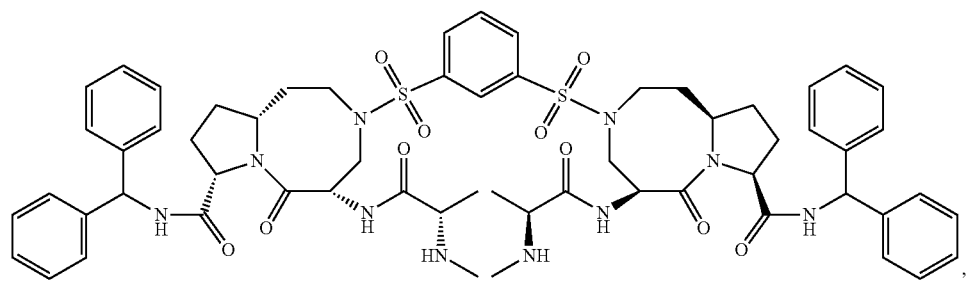 [SMILES: CN[C@@H](C)C(=O)N[C@H]1CN(S(=O)(=O)c2cccc(S(=O)(=O)N3CC[C@H]4CC[C@@H](C(=O)NC(c5ccccc5)c5ccccc5)N4C(=O)[C@@H](NC(=O)[C@H](C)NC)C3)c2)CC[C@H]2CC[C@@H](C(=O)NC(c3ccccc3)c3ccccc3)N2C1=O]
or a pharmaceutically acceptable salt thereof.
* * * * *